US011741277B2

(12) United States Patent
Dayal et al.

(10) Patent No.: US 11,741,277 B2
(45) Date of Patent: Aug. 29, 2023

(54) PREDICTIVE MODELING PLATFORM FOR SERIAL CASTING TO CORRECT ORTHOPEDIC DEFORMITIES

(71) Applicant: BabySteps Orthopedics Inc., Wilmington, DE (US)

(72) Inventors: Anuradha Dayal, Washington, DC (US); Reza Monfaredi, Rockville, MD (US); Kevin Cleary, Potomac, MD (US); Matthew Oetgen, Chevy Chase, MD (US)

(73) Assignee: BabySteps Orthopedics Inc., Wilmington, DE (US)

( * ) Notice: Subject to any disclaimer, the term of this patent is extended or adjusted under 35 U.S.C. 154(b) by 8 days.

(21) Appl. No.: 17/073,183

(22) Filed: Oct. 16, 2020

(65) Prior Publication Data

US 2021/0042458 A1 Feb. 11, 2021

Related U.S. Application Data

(63) Continuation-in-part of application No. 16/864,099, filed on Apr. 30, 2020.

(Continued)

(51) Int. Cl.
 *G06F 30/27* (2020.01)
 *G06T 19/20* (2011.01)
(Continued)

(52) U.S. Cl.
 CPC ............ *G06F 30/27* (2020.01); *A61F 5/0127* (2013.01); *G06F 30/23* (2020.01); *G06T 19/20* (2013.01);

(Continued)

(58) Field of Classification Search
 CPC .......... G06F 30/00; G06F 30/27; G06F 30/23; G06F 2111/16; G16H 50/50; G16H 30/40;
 (Continued)

(56) References Cited

U.S. PATENT DOCUMENTS

| 7,386,428 B1 * | 6/2008 | Hallquist | ................ G06F 30/23 |
| | | | 703/2 |
| 7,569,023 B2 | 8/2009 | Dobbs | |

(Continued)

FOREIGN PATENT DOCUMENTS

WO 2019/157486 A1 8/2019

OTHER PUBLICATIONS

U.S. Appl. No. 16/864,099, filed Apr. 30, 2020, 2020-0349308, Published.

(Continued)

*Primary Examiner* — Charles L Beard
(74) *Attorney, Agent, or Firm* — McCarter & English, LLP

(57) ABSTRACT

A system and method are provided herein for modeling of force vectors for serial casts to correct orthopedic deformities includes a camera configured to capture a three-dimensional image of the deformity, a computing device programmed to generate a three-dimensional model of the deformity based on the image of the deformity, determine the boundary conditions for the deformity based on the three-dimensional image of the deformity, and generate force vectors for a series of casts to correct the deformity. In exemplary embodiments, the system can print a series of casts to correct the deformity.

14 Claims, 17 Drawing Sheets

Related U.S. Application Data

(60) Provisional application No. 62/928,808, filed on Oct. 31, 2019, provisional application No. 62/841,012, filed on Apr. 30, 2019.

(51) Int. Cl.

| | |
|---|---|
| *G06F 30/23* | (2020.01) |
| *A61F 5/01* | (2006.01) |
| *G16H 30/40* | (2018.01) |
| *G06F 111/16* | (2020.01) |

(52) U.S. Cl.
CPC .......... *G16H 30/40* (2018.01); *G06F 2111/16* (2020.01); *G06T 2210/41* (2013.01)

(58) Field of Classification Search
CPC ... G16H 20/30; A61F 2002/5049; A61F 5/01; A61F 5/0127; A61F 5/0111; A61F 5/14; A43D 2200/60; A43D 1/02; G06T 19/20; G06T 2207/10088; G06T 17/00; G06T 2200/04; G06T 2207/30052; G06T 2219/2021; G06T 2219/20; G06T 2207/10081; G06T 2207/10096; G06T 2210/41; G06T 30/00; G06N 3/08
See application file for complete search history.

(56) References Cited

U.S. PATENT DOCUMENTS

| | | | | |
|---|---|---|---|---|
| 8,083,703 | B2 | 12/2011 | Daizade | |
| 8,180,605 | B1* | 5/2012 | Zhu | G06F 30/23 703/2 |
| 8,814,815 | B2 | 8/2014 | DeHeer et al. | |
| 9,361,413 | B1* | 6/2016 | Bout | G06F 30/13 |
| 9,626,466 | B2* | 4/2017 | Yang | G06F 30/23 |
| 10,558,770 | B1* | 2/2020 | Kanthasamy | G06T 17/20 |
| 10,915,678 | B1* | 2/2021 | Schafstall | G06F 17/13 |
| 11,488,062 | B1* | 11/2022 | Earthman | G06N 20/00 |
| 2006/0070260 | A1* | 4/2006 | Cavanagh | G16H 50/50 36/44 |
| 2008/0275677 | A1* | 11/2008 | Landon | G06F 30/23 703/2 |
| 2009/0306801 | A1* | 12/2009 | Sivak | A61F 5/0113 700/118 |
| 2011/0087465 | A1* | 4/2011 | Mahfouz | G06T 7/33 703/2 |
| 2013/0226059 | A1* | 8/2013 | Morris | A61F 5/0111 602/27 |
| 2014/0180185 | A1* | 6/2014 | Zachariasen | B33Y 50/02 602/5 |
| 2014/0180648 | A1* | 6/2014 | Borrvall | B60R 21/16 703/2 |
| 2016/0022466 | A1* | 1/2016 | Pedtke | A61F 5/0127 700/98 |
| 2016/0101571 | A1* | 4/2016 | Schouwenburg | B33Y 50/00 602/5 |
| 2016/0101572 | A1* | 4/2016 | Schouwenburg | B33Y 80/00 602/5 |
| 2016/0331071 | A1* | 11/2016 | Kane | A43B 17/00 |
| 2017/0091411 | A1* | 3/2017 | Schoenecker | G16H 20/30 |
| 2017/0116360 | A1* | 4/2017 | Han | G06F 30/23 |
| 2017/0228859 | A1* | 8/2017 | Schouwenburg | A43B 17/02 |
| 2017/0337307 | A1* | 11/2017 | Oancea | G06F 30/23 |
| 2017/0360578 | A1 | 12/2017 | Shin et al. | |
| 2017/0372480 | A1* | 12/2017 | Anand | G06T 7/11 |
| 2018/0157228 | A1* | 6/2018 | Spector | A43B 17/006 |
| 2018/0177624 | A1* | 6/2018 | Vlasic | A43B 7/141 |
| 2018/0247158 | A1* | 8/2018 | Yang | G06V 10/76 |
| 2019/0050506 | A1* | 2/2019 | Umetani | G06N 3/02 |
| 2019/0231578 | A1* | 8/2019 | Ranganathan | A61F 5/14 |
| 2019/0261733 | A1* | 8/2019 | Schouwenburg | A43B 7/143 |
| 2019/0283394 | A1* | 9/2019 | Ashcroft | A43B 5/06 |
| 2020/0151594 | A1* | 5/2020 | Schwartz | G06N 20/00 |
| 2020/0214870 | A1* | 7/2020 | Washizu | A61F 5/01 |
| 2020/0238626 | A1* | 7/2020 | Bleicher | A61F 5/14 |
| 2020/0245724 | A1* | 8/2020 | Kobe | A61B 6/032 |
| 2020/0272139 | A1* | 8/2020 | Rakuff | G06N 3/084 |
| 2020/0349308 | A1* | 11/2020 | Dayal | G06F 30/23 |
| 2020/0357508 | A1* | 11/2020 | Deleu | G16H 50/50 |
| 2021/0103685 | A1* | 4/2021 | Makem | G06T 17/205 |
| 2021/0145608 | A1* | 5/2021 | Herr | A61B 8/0825 |
| 2021/0177089 | A1* | 6/2021 | Schouwenburg | A43B 7/143 |
| 2021/0315323 | A1* | 10/2021 | Hakkala | A61B 5/107 |
| 2022/0068016 | A1* | 3/2022 | Raz | G06T 17/00 |
| 2022/0131975 | A1* | 4/2022 | Krishnan | G06F 40/30 |
| 2022/0318591 | A1* | 10/2022 | Haderbache | G06N 3/04 |

OTHER PUBLICATIONS

Ganesan et al., A novel 3D evaluation method for assessing bone to bone relationships in clubfoot. Eur Rev Med Pharmacol Sci. Mar. 2019;23(5):1882-1890.

Gozar et al., Finite-element-based 3D computer modeling for personalized treatment planning in clubfoot deformity Case report with technique description. Medicine (Baltimore). Jun. 2018;97(24):e11021, 7 pages.

Gozar et al., Medical Use of Finite Element Modeling of the Ankle and Foot. Journal of Interdisciplinary Medicine. Jan. 29, 2018, 5 pages, pre-publicaiton edition. DOI: 10.1515/jim-2018-0001.

Jain et al., Biomodeling of clubfoot deformity of babies. Rapid Prototyping Journal. May 29, 2009; 15(3):164-170.

Khas et al., Development of an orthosis for simultaneous three-dimensional correction of clubfoot deformity. Clin Biomech (Bristol, Avon). Jan. 2018;51:67-75.

Manak et al., 3D Modeling of Shape Geometry of Talus of Clubfoot (CTEV). Foot Ankle Stud. 2018;2(1):1012, 5 pages.

International Search Report and Written Opinion for Application No. PCT/US2020/058597, dated Feb. 11, 2021, 13 pages.

International Preliminary Report on Patentability for Application No. PCT/US2020/058597, dated May 12, 2022, 10 pages.

Desai et al., Bracing in the treatment of children with clubfoot: past, present, and future. Iowa Orthop J. 2010;30:15-23.

Ganesan et al., Developing a Three-Dimensional (3D) Assessment Method for Clubfoot—A Study Protocol. Front Physiol. Jan. 4, 2018;8:1098, 11 pages.

Giesberts et al., Ten cold clubfeet. Acta Orthop. Oct. 2018;89(5):565-569.

Grabcad Community, 3D printed cast for the Ponseti Method. Retrieved online at: https://grabcad.com/library/3d-printed-cast-for-the-ponseti-method-1. 4 pages, Jan. 28, 2019.

Howren et al., Early ultrasonographic evaluation of idiopathic clubfeet treated with manipulations, casts, and Botox (®): a double-blind randomized control trial. J Child Orthop. Feb. 2015;9(1):85-91.

Krivonlak et al., 3D Printed Custom Orthotic Device Development: A Student-driven Project. 2017 ASEE Annual Conference & Exposition. 12 pages, Jun. 2017.

Nichols, The Ponseti Method: Bracing Phase. KidsHealth, retrieved online at: https://kidshealth.org/en/parents/ponseti-bracing.html. 4 pages, Feb. 2022.

Savonen et al., Open-Source Three-Dimensional Printable Infant Clubfoot Brace. Journal of Prosthetics and Orthotics. 21 pages, (2019). pre-print. doi: 10.1097/JPO.0000000000000257.

Steps Clubfoot Care, The clubfoot brace. Retrieved online at: https://steps.org.za/bracewear/. 3 pages, (2016).

Wallander, Congenital clubfoot. Aspects on epidemiology, residual deformity and patient reported outcome. Acta Orthop Suppl. Feb. 2010;81(339):1-25.

* cited by examiner

Sagittal plane evaluation of equinus

Frontal plane evaluation of varus

Horizontal plane evaluation of derotation of the calcaneopedal block

Horizontal plane evaluation of forefoot relative to hindfoot

| Simulation | DIFFERENCE EQUINUS (DEGREES) Equinus (real) - Equinus (simulated) | DIFFERENCE DE-ROTATION (DEGREES) De-rotation (real) - de-rotation (simulated) | AVERAGE DIFFERENCE BETWEEN POINT CLOUDS (mm) (real-simulated) |
|---|---|---|---|
| 1 | 0.74 | 0.035 | 2.31 |
| 2 | 0.2 | 0.1 | 2.27 |
| 3 | 0.1 | 0.3 | 1.96 |
| 4 | 0.9 | 0.4 | 2.22 |
| 5 | 0.13 | 0.05 | 2.24 |
| 6 | 0.27 | 0.03 | 2.19 |
| 7 | 0.52 | 0.12 | 2.08 |
| 8 | 0.77 | 0.71 | 2.1 |
| 9 | 0.65 | 0.39 | 3.11 |
| 10 | 1 | 0.91 | 3.04 |
| 11 | 1.6 | 0.46 | 3.08 |
| 12 | 0.83 | 0.94 | 2.84 |
| 13 | 1.59 | 0.69 | 2.59 |
| 14 | 0.68 | 0.62 | 2.52 |
| 15 | 1.11 | 0.39 | 2.34 |
| 16 | 0.44 | 0.79 | 2.73 |
| 17 | 0.43 | 0.67 | 2.42 |
| 18 | 1.41 | 0.84 | 2.03 |
| 19 | 0.7 | 0.96 | 1.61 |
| 20 | 1 | 0.62 | 1.31 |
| 21 | 0.8 | 0.14 | 1.65 |
| 22 | 0.29 | 0.26 | 1.86 |
| 23 | 0.16 | 0.56 | 2.89 |
| 24 | 0.85 | 0.49 | 2.03 |
| 25 | 1.05 | 1.1 | 2.58 |
| 26 | 1.52 | 1.15 | 3.46 |
| 27 | 1.23 | 1.66 | 2.65 |
| 28 | 1.22 | 1.2 | 2.4 |
| 29 | 1.39 | 1.08 | 2.16 |
| 30 | 1.62 | 1.38 | 1.93 |
| 31 | 1.01 | 1.2 | 1.77 |
| 32 | 1.81 | 1.88 | 2.3 |
| 33 | 1.41 | 1.38 | 2.12 |
| 34 | 1.91 | 1.07 | 1.93 |
| 35 | 1.12 | 1.01 | 2.21 |
| 36 | 1.14 | 1.41 | 1.85 |
| OVERALL AVERAGE | 0.93 | 0.75 | 2.31 |

PREDICTIVE MODELING PLATFORM FOR SERIAL CASTING TO CORRECT ORTHOPEDIC DEFORMITIES

CROSS REFERENCE TO RELATED APPLICATIONS

The present application is a continuation-in-part of the U.S. patent application Ser. No. 16/864,009 filed on Apr. 30, 2020, which in turn claims the benefit of U.S. Provisional Patent Application No. 62/841,012, filed on Apr. 30, 2019, both applications are incorporated herein by reference in their entirety. The present application also claims priority to U.S. Provisional Patent Application No. 62/928,808, filed on Oct. 31, 2019 which is also incorporated herein by reference in its entirety.

BACKGROUND

Musculoskeletal disorders such as neuromuscular (NM), musculoskeletal (MSK) disorders can be congenital or acquired. Some musculoskeletal disorders can be treated in pediatric and adult populations through serial casting. Conventionally, treating musculoskeletal disorders using serial casting can be difficult because of difficulties with access to care and the relative subjectivity of the treatment. For example, common pediatric orthopedic deformities such as Talipes equinovarus or congenital talipes equinovarus (commonly called clubfoot) have been difficult to treat. In the case of clubfoot, the current standard of care afforded to correct this skeletal deformity is the Ponseti serial casting methodology, in which the deformity is corrected using a weekly series of casts. Limitations of this method include the need for highly trained surgeons proficient in this method and frequent weekly visits to the orthopedic surgeon for placement of the casts. Even when skilled doctors trained in the method are available, there is a lot of variability and subjectivity in determining the next step of the serial cast. Variability in casting technique and inability to predict treatment length lead to difficulties in standardization of the treatment course of serial clubfoot correction. Similar difficulties exist with respect to treating patients with other congenital NM, congenital MSK, acquired NM, and acquired MSK disorders using serial casts.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1D is a data table comparing simulation data for a cast geometry as taught herein with actual data for a formed cast in accordance with various embodiments taught herein;

DETAILED DESCRIPTION

Figure 1A:
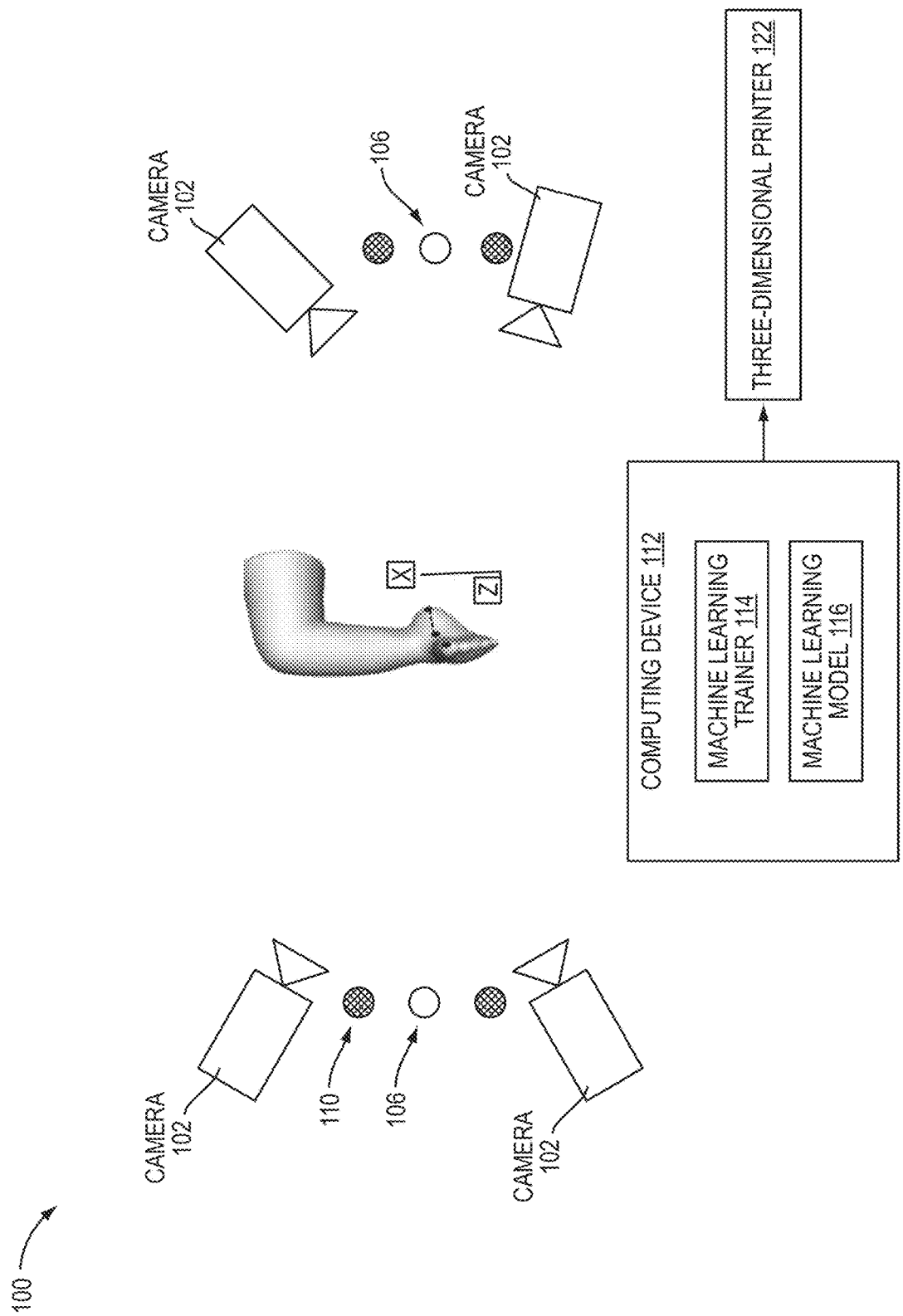
FIG. 1A is a block diagram illustrating a system for modelling force vectors for serial casts to correct orthopedic deformities in accordance with various embodiments taught herein.

Serial casting corrects a three-dimensional musculoskeletal deformity, neuromuscular deformity or both through periodic manipulation of the deformity. For example, in the case of deformity of clubfoot, the congenital musculoskeletal deformity is corrected through weekly manipulation of the deformity of the foot in a step-wise process using serial casts. Often times correction is in multiple three-directional planes simultaneously. Conventionally, this manipulation is a very manual process, labor intensive and embodies an imprecise prediction of subsequent steps and outcomes. Although, computer modelling for serial casts to correct musculoskeletal deformity, neuromuscular deformity or both exists, the conventional computer modeling requires a linear approach of approximating a series of points and lines to determine a specific direction in which a cast in the series of casts applies a force to the deformity. However, the linear approach does not account for the three-dimensional deformities of the clubfoot within the cavus, adductus, varus, equinus and derotational elements.

Embodiments of the present disclosure include systems and methods for modelling a set of force vectors for a cast or a next cast in a series of casts to correct the musculoskeletal deformity, the neuromuscular deformity or both that overcome the difficulties and problems described herein with respect to conventional serial casting techniques. In exemplary embodiments, the system includes a processor that executes machine readable instructions to receive an image of the deformity. In turn, the processor generates a three-dimensional model of the deformity based on the image of the deformity. Further, the processor determines a deviation between a three-dimensional stereo-typical anatomical alignment and the three-dimensional model of the deformity (i.e., boundary conditions of the deformity) and generates a next intermediate anatomical alignment in a series of intermediate anatomical alignments for correcting the deviation based on a machine learning model trained on a plurality of prior patient records. The processor also simulates a plurality of trial force vectors for a next cast to correct the deformity to the next intermediate anatomical alignment. The simulation generates a projected anatomical alignment post-treatment with the next cast on the deformity using finite element analysis for each of the trial force vectors, and identifies a next force vector from the plurality of trial force vectors that minimizes the difference between the projected anatomical alignment and the next intermediate anatomical alignment, such that using the next force vector for the next cast results in an average difference in the range of 2 mm to 20 mm on a point to point comparison between a point in a point cloud of the next cast and a corresponding point in a point of a point cloud of a prior cast for a similar correction based on prior patient data.

In exemplary embodiments, the camera is an array of cameras, an x-ray imager, an ultrasound scanner, a three-dimensional scanner, an magnetic resonance imaging device, a CT scan or a combination thereof. For example, the camera can be a depth detection camera or include a light detection and ranging (LIDAR) sensor that produces a point cloud of the deformity.

In exemplary embodiments, the system can determine boundary conditions for the deformity based on the three-dimensional image of the deformity and medical data from a plurality of persons. The medical data from the plurality of persons can include images, image data, data and information about stereo-typical anatomical alignment, anatomical alignment of prior patient deformities prior to correction, intermediate anatomical alignment of patient deformities during correction and final alignment of patient deformities post correction. In exemplary embodiments, the medical data for prior patient deformities can be derived from discarded casts of prior patients used during their treatment and scans of the patient deformities during their treatment. In some embodiments, the medical data for prior patient deformities can be derived from medical records generated during patient visits such as notes from the doctor, 2-dimensional images such as x-rays, measurements of force vectors such as spasticity and the like. In exemplary embodiments, the medical data can be converted to a point cloud that represents the three-dimensional model of the anatomical alignment(s) for the patient, the stereo-typical person or both.

In exemplary embodiments, the plurality of prior patient data includes an original image of the deformity of the patient(s), intermediate images of the deformity of the patient(s) and an image of the final corrected deformity of the patient(s). In some exemplary embodiments the plurality of prior patient data includes data generated from a plurality of scans or images of prior discarded casts of patients used during treatment of the deformity.

In exemplary embodiments, to simulate the plurality of trial force vectors for the next cast the system can generate a series of forces at a plurality of nodes in the three-dimensional model of the deformity and determine a resulting change in the anatomical alignment of the deformity after a certain period of time based on the application of the series of forces at the nodes.

In exemplary embodiments, to select the next force vector from the plurality of trial force vectors the system can determine which of the plurality of trial force vectors minimizes the deviation between the projected anatomical alignment and the next intermediate anatomical alignment based on a finite element analysis machine learning model.

The finite element analysis machine learning model is trained on medical data that can include next force vectors that correspond to a points on a point cloud of the deformity that were selected form the plurality of trial vectors during treatments in prior patients.

In exemplary embodiments, to select the next force vector the system can minimize the deviation between the projected anatomical alignment and the next intermediate anatomical alignment in multiple directions to reduce the deviation between the three-dimensional stereo-typical anatomical alignment and the three-dimensional model of the deformity in multiple directions simultaneously after the next cast is applied to the deformity.

In exemplary embodiments, to select the next force vector the system can minimize the difference between the projected anatomical alignment and the next intermediate anatomical alignment in a direction with the maximum deviation between the three-dimensional stereo-typical anatomical alignment and the three-dimensional model of the deformity after the next cast is applied to the deformity.

Referring now to FIG. 1A which illustrates a system 100 to capture an image of the deformity according to the present disclosure is provided. The system 100 includes a camera 102 (shown in FIG. 1A as an array of cameras) configured to capture a three-dimensional image of the deformity and a plurality of light sources 106. In an exemplary embodiment the system 100 can include a calibration target 110. Examples of the calibration target 110 include checkerboard patterns, socks with or without identification patterns and the like. For example, the calibration target 110 can be a checkerboard pattern that can attached on a flat board that can move relative to the camera 102 to acquire calibration images of the calibration target 110 with various poses relative to the camera 102. In an exemplary embodiment, the system 100 can use a calibration target 110 for subjects where the deformity is kept relatively still. The use of a calibration target with multiple cameras allows the system 100 to capture a three-dimensional images and compensate for movement.

In an exemplary embodiment, the camera 102 can be an array of cameras. The system 100 can generate a three-dimensional image of the deformity by stitching all the images from the array of cameras. In an exemplary embodiment, the camera can be a digital camera, or a video camera, an ultrasound imaging system, MRI or a CT scan. The system 100 can compensate for movement of the subject using image processing to obtain an accurate representation of the deformity in three-dimensions. In exemplary embodiments, the camera 102 can capture be a depth sensing camera (e.g., Microsoft Kinect™), which produces a point cloud of the deformity. In some embodiments, the system 100 can convert a three-dimensional image of the deformity into a point cloud. In exemplary embodiments, the camera 102 can capture imagery data for generating a point cloud of the deformity based on discarded casts used during treatment of a patient. In an exemplary embodiment, the system 100 can acquire an image of the deformity from a mobile device such as a phone or tablet camera. The system 100 can receive an image captured from a mobile device that captures the deformity from different angles. The system 100 can then stitch the images together to create a three-dimensional image.

In an exemplary embodiment, the system 100 can determine a deviation or average deviation on a point by point basis between a three-dimensional model of the deformity and the three-dimensional stereo-typical anatomical alignment of the human anatomy in question. For example, the system 100 can include a database or corpus storing medical data of the individuals. The medical data of the individuals can include three-dimensional models of stereo-typical anatomical alignment of the human anatomy, three-dimensional models of deformities that deviate from the stereo-typical anatomical alignment based on medical records of prior patients with deformities and the like.

In exemplary embodiments, the system 100 can use one or more point clouds representing a three dimensional model of a cast or deformity to perform shape analysis instead of the more conventional mesh models. Traditionally, shape analysis methods have operated on solid and surface models of objects, especially tessellated models (i.e., triangular mesh surface models). Shape analysis is concerned with understanding the shape of models geometrically, topologically, and relationally. In some embodiments, the system 100 can use shape analysis to group the deformities in the database based on the type of the deformity, segment the deformities based on the shape into sub-shapes, and find complementary deformities based on the shape of the deformity. For example, the system 100 can query the database with the medical data using a point cloud of a deformity that has been acquired to return a matching point cloud of a similar deformity.

The system 100 can generate a next intermediate anatomical alignment in a series of three-dimensional alignments based on a machine learning model 116 trained on prior patient data from the database or corpus. In order to train the machine learning model, the system 100 can include a computing device 112. The computing device 112 can include a machine learning trainer 114 to generate the machine learning model 116. In an exemplary embodiment, the system 100 can generate a machine learning model based on supervised learning, unsupervised learning or reinforcement learning. In an exemplary embodiment, the machine learning trainer 114 can be implemented as a machine learning computing device that also stores and allows use of the machine learning model 116. The machine learning trainer 114 can analyze a set of training data that includes a classification of the data that the machine learning trainer 114 can use to calibrate its algorithm to identify what lies within a class or is outside a class. For example, a convolutional neural network or deep learning neural network trained on three-dimensional models of club foot can classify a new three-dimensional model acquired by the system 100 based on the trained machine learning model 116.

The system 100 can generate the machine learning model 116 that can be used to generate a next intermediate three-dimensional anatomical alignment in a series of intermediate three-dimensional anatomical alignments to correct the orthopedic deformities. For example, the system 100 can receive training data that includes medical data of patients who were treated to correct a deformity such as three-dimensional images of the uncorrected deformity, three-dimensional images of the intermediate anatomical alignments achieved during treatment of the deformity, and the three-dimensional images of the final corrected anatomical alignment achieved after treatment. In some embodiments, the training data can also include three-dimensional anatomical alignments of stereo-typical persons. In some embodiments, the training data can be generated from discarded casts of patients who were treated for a deformity. The system 100 can use the prior discarded casts to approximate the deformity at each stage of the correction process where the three-dimensional images of the foot are not available. When treating clubfoot, the training data can include patient data obtained during the treatment of a patient using the Ponseti method. In an exemplary embodiment, machine learning models analyze data from a plurality of prior patients to identify mean shapes and shape variations. The system 100 can then determine boundary conditions of the machine learning model 116 to classify a new three-dimensional surface model of a deformity acquired from a new patient to determine whether the deformity of the new patient falls within the boundary of a particular type of deformity or to identify a similar deformity in the prior medical records that closely match the shape, type or both. The system 100 can then determine a next three-dimensional intermediate anatomical alignment in a series of anatomical alignments based on the prior identified deformity.

In an exemplary embodiment, the machine learning model 116 can be trained to output the desired correction angles to correct the deformity to the next intermediate alignment, i.e., the desired angles of correction that will result in the next three-dimensional anatomical alignment for correcting the deformity.

In an exemplary embodiment, the system 100 can train the machine learning model based on prior patient data for a plurality of patients such an original three-dimensional image of the deformity, images of intermediate stages of correction of the deformity and the final image of the corrected deformity. In exemplary embodiments, the system can use three-dimensional scans of prior discarded casts of patients to determine the original deformity, stages of correction of the deformity and the final corrected deformity.

The system 100 can simulate trial force vectors for a next cast that can correct the deformity to the next intermediate anatomical alignment using finite element analysis at the nodes of the three-dimensional model of the deformity. The system 100 can simulate the projected anatomical alignment for each trial force vector post-treatment with the next cast based on finite element analysis of the three-dimensional model of the deformity. For example, the system 100 can apply finite element analysis with the trial force vectors acting at the nodes of the three-dimensional model of the deformity to determine the projected anatomical alignment post-treatment with the next cast.

Figure 1B:
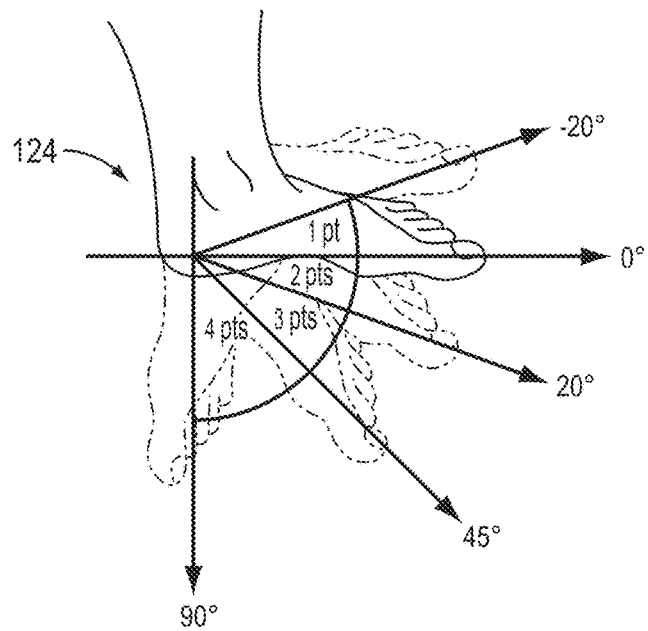
FIG. 1B is an illustration of the corrective vector forces for correcting an orthopedic deformity in accordance with various embodiments taught herein.
Figure 1B:
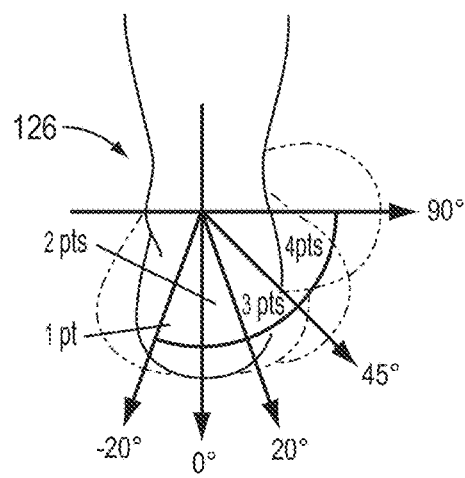
Figure 1B:
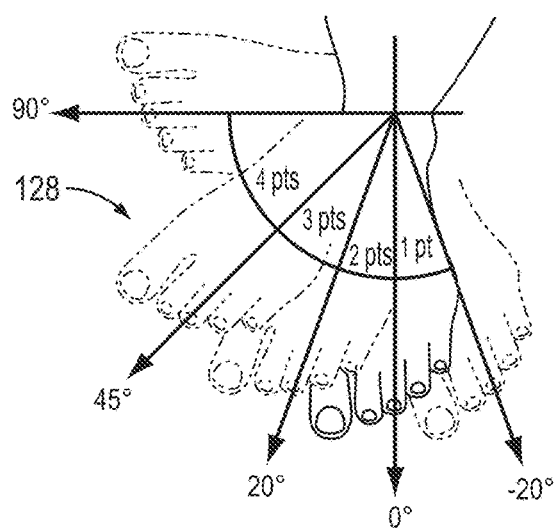
Figure 1B:
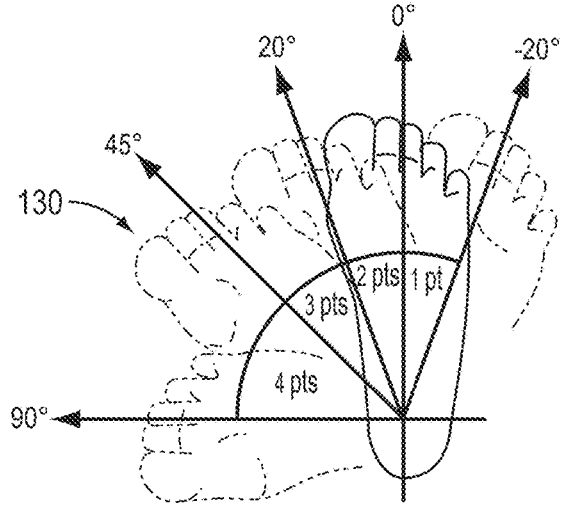

In an exemplary embodiment, the system 100 can generate training data for the machine learning model based on modelling and analysis software such as ANSYS. Modelling and simulation software can be used to deform a 3D three-dimensional CAD model of a normal foot into a plurality of virtually generated CAD models (e.g., 500 models), for example, clubfoot CAD models, with different degrees and angles of deformity potentially seen during the correction sequence. In an embodiment, system 100 can use supervised learning and the system 100 can receive inputs from an orthopedic surgeon (e.g., pediatric orthopedic surgeon) to review the models for accuracy. The system 100 can export the CAD models as point cloud models for anatomical classification/labeling of the generated models for the machine learning model. The system 100 can use the point cloud model of the foot to identify the severity of the clubfoot deformity by determining the amount of deviation of the foot with respect to normal pose in four different directions as shown in FIG. 1B. FIG. 1B illustrates the deformities in clubfoot such as the equinus deformity 124, the varus deformity 126, the calcancopedal derotation 128 and the horizontal plane deformity relative to hindfoot 130. The system 100 can capture the variation in these deformities using the camera 102. In an exemplary embodiment, the machine learning model can be evolved to improve the accuracy of the model over time.

The system 100 can use a deep learning method such as a PointNet to process the point cloud models. PointNet is an open source platform for classification of point cloud models. Since the point cloud model is randomly oriented, they use a bounding box that fits into the model, and normalizes the point cloud to always align the point cloud model in a certain direction before feeding it into the deep learning network as input datasets. The system 100 can use PointNet to classify different stages of an orthopedic skeletal deformity, for example, clubfoot deformity. In an exemplary embodiment, the system 100 can use the point cloud CAD models generated using simulation software to train a deep learning network to objectively classify and label each patient's unique foot deformity compared to a normal foot. The system 100 can then train the network to predict the cast series for each subject patient in this study. The system 100 can use supervised learning based on inputs obtained by presenting an orthopedic skeletal deformity model, for example, a clubfoot model, to one or more orthopedic surgeons. In an exemplary embodiment, the models can be presented with a selection of candidate foot correction models (e.g., out of five hundred foot models) that is the next in the correction series based on the Ponseti method. The system 100 can then receive inputs from the doctors on a consensus basis and select the next correction phase out of the selection of candidate foot models (e.g., 10 models). Over the course of multiple rounds of selection (e.g., 500 rounds) the system 100 trains the deep learning network to search the training dataset and output the subsequent cast for deformity correction.

In an exemplary embodiment, the system 100 can generate an STL file for three-dimensional printing using a three-dimensional printer 122.

The system 100 can select a next force vector for the next cast from the trial force vectors by identifying the force vector that minimizes the difference between the projected anatomical alignment and the next intermediate anatomical alignment. In accordance with the teachings herein, using the next force vector in the next cast results in an average difference in the range of 2 mm to 20 mm between a point in a point cloud of the next cast and a corresponding point in a point cloud of a prior cast for a similar correction in a prior patient data. The system 100 can determine the shape and dimensions of the next cast within a range of 2 mm to 20 mm when compared with a trained and skilled doctor with years of experience performing the casting using subjective parameters.

In exemplary embodiments, the system 100 can select a next force vector for the next cast from the trial force vectors by identifying the force vector that minimizes the difference between the projected anatomical alignment and the next intermediate anatomical alignment. In accordance with the teachings herein, the next force vector for the next cast results in an average difference in the range of 0.5 degrees to 4 degrees between the angles in a point cloud of the next cast and the corresponding angles in a point cloud of a prior cast for a similar correction in a prior patient data.

Figure 1C:
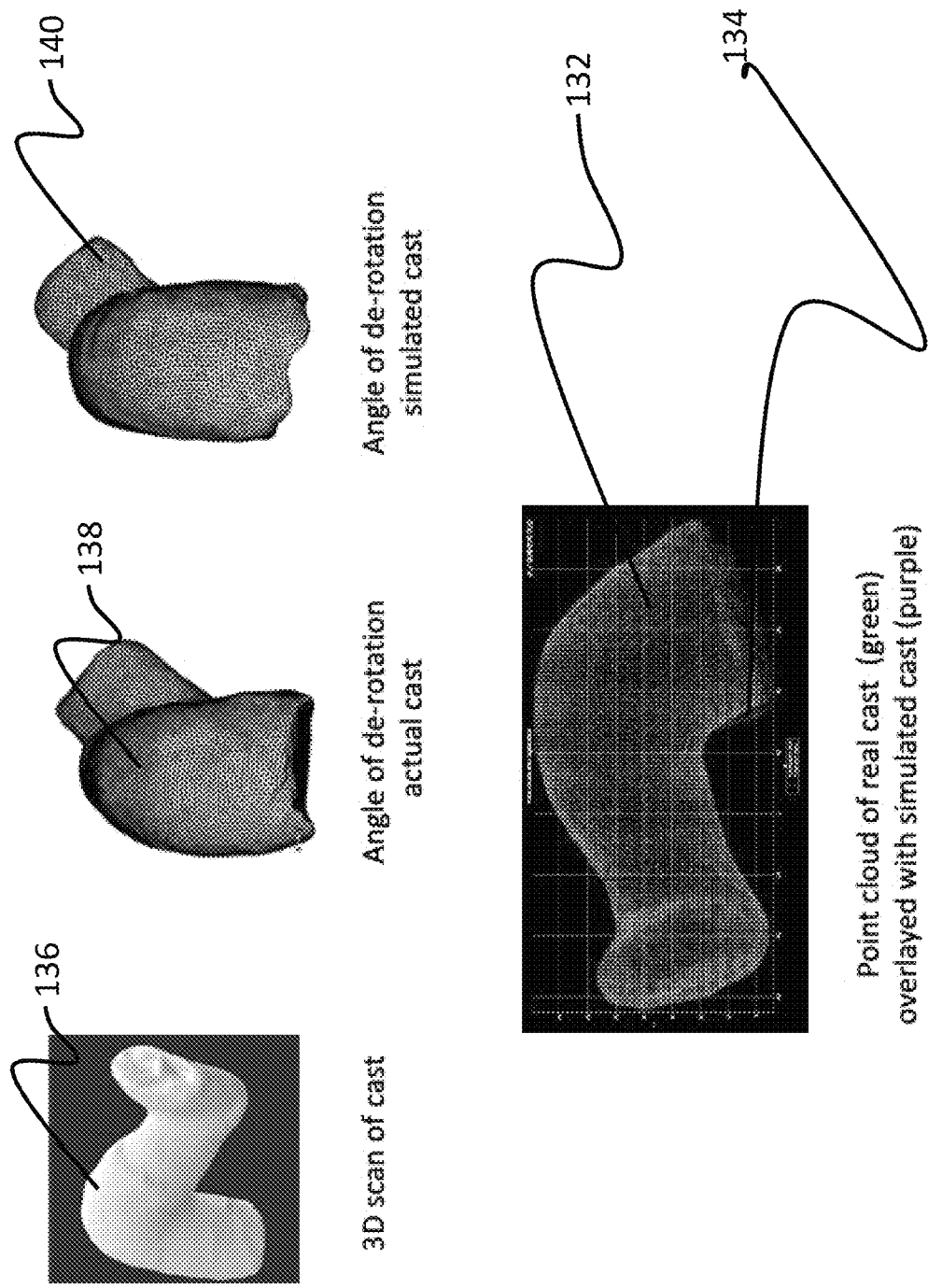
FIG. 1C is an illustration of a point cloud of a simulated cast superimposed on a point cloud of a real cast in accordance with various embodiments taught herein.

Referring to FIG. 1C the system 100 can determine the dimensions and shape of the next cast in a series of casts for correcting the deformity to a high degree of accuracy without the subjective judgement of a highly skilled doctor. The system 100 can generate a point cloud 138 of the three-dimensional scan of the cast 136 of a prior patient as shown in FIG. 1C. The system 100 can then determine a simulated angle of derotation 140. For a given deformity FIG. 1C illustrates a point cloud of the simulated cast 134 generated by the system 100 when compared to the point cloud of a real cast 132 placed by a highly skilled orthopedic to correct the deformity. When using the system 100 to generate the next cast, the average difference between the dimensions of the point cloud of the simulated cast 134 and the point cloud of the real cast 132 can be in the range of 2 mm to 20 mm on a point to point basis between corresponding points in a point cloud of the simulated next cast 134 and a point cloud of a prior cast 132 for a similar correction in a prior patient data. When using the system 100 to generate the next cast, the average difference can be in the range of 0.5 degrees to 4 degrees between the angles in a point cloud of the simulated next cast 134 and the corresponding angles in a point cloud of a prior cast 132 for a similar correction in a prior patient. In an exemplary embodiment, the average difference between the angles of the real 132 and simulated casts 134 was 0.93 degrees for equinus and 0.74 degrees for de-rotation. In exemplary embodiments, the average difference between corresponding points of the real cast 132 and simulated casts 134 in the respective three-dimensional point clouds was 2.305 mm.

Referring to FIG. 1D the table represents the difference between the angles on the simulated next cast 134 and the corresponding angles in a point cloud of a prior cast 132 for similar correction in a prior patient. For example, the table illustrates that the difference between the angles in a point cloud of the simulated next cast 134 and the corresponding angles in a point cloud of a prior cast 132 for Equinus correction 136, de-rotation correction 138 and the average difference 140 between point clouds.

Figure 2:
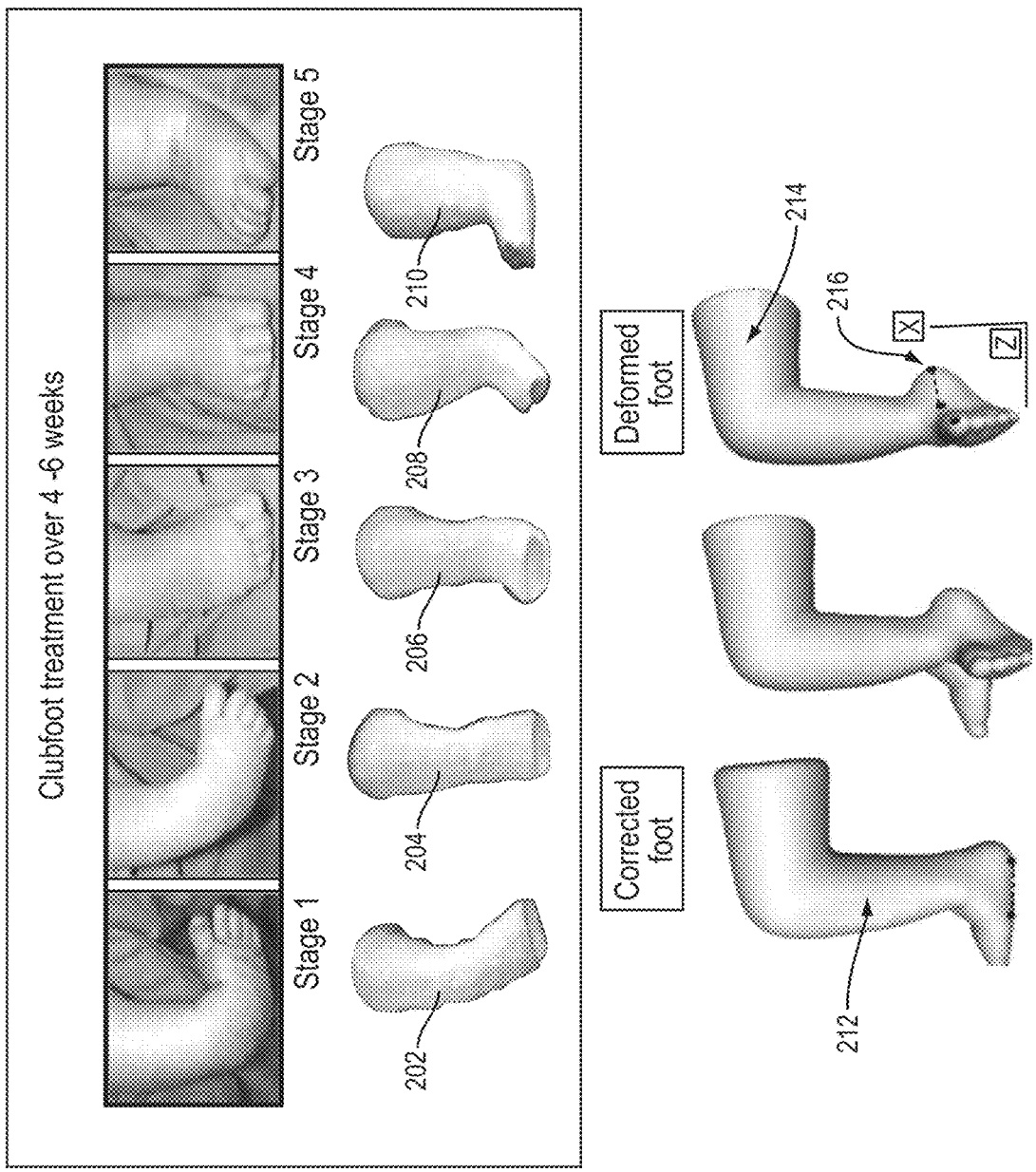
FIG. 2 is an illustration of a series of casts generated to correct the orthopedic deformity in accordance with various embodiments taught herein.

Referring to FIG. 2. the system 100 can generate a cast or a series of casts as shown in FIG. 2 to correct the orthopedic deformity. In an exemplary embodiment the system 100 can generate a cast or a series of casts that can be three-dimensional printed. The system 100 determines a force vector or a set of force vectors to correct the orthopedic deformity based on three-dimensional imagery of the deformity and the machine learning model 116 can generate the next intermediate anatomical alignment for correcting the deviation. In an exemplary embodiment, next intermediate anatomical alignment can be the desired corrected angles for correcting the deformity in the next cast. In an exemplary embodiment, the system 100 can determine the shape and geometry of a cast or a series of casts 202-210 that exert the determined force vector or set of force vectors that are tailored to the patient. In an exemplary embodiment, the system 100 can determine the force vectors for the series of casts 202-210 to correct the deformed foot 214 with three-dimensional deformities shown along the x, y and z axis to arrive at the corrected foot 212. In an exemplary embodiment, the system 100 selects the force vector or set of force vectors such that the right areas 216 that are structurally designed in normal foot of children to distribute the load when walking is in the same plane and perform the load bearing function once corrected.

It can be appreciated that, depending on the baseline anatomical shape and arrangement and an anatomical rearrangement goal, or target, an appropriate serial casting strategy can be developed. For instance, not all patients may need the same number of casts. In fact, it may be that a patient requires fewer casts as deformities to the internal anatomy of the foot may be less severe. In other cases, the deformity to the underlying anatomy may be significant and more casts may be prescribed. Being able to combine this internal information, however, with exterior data of the surface of the foot allows for generation of three-dimensional printed 'corrective' casts that are patient-specific.

Figure 3A:
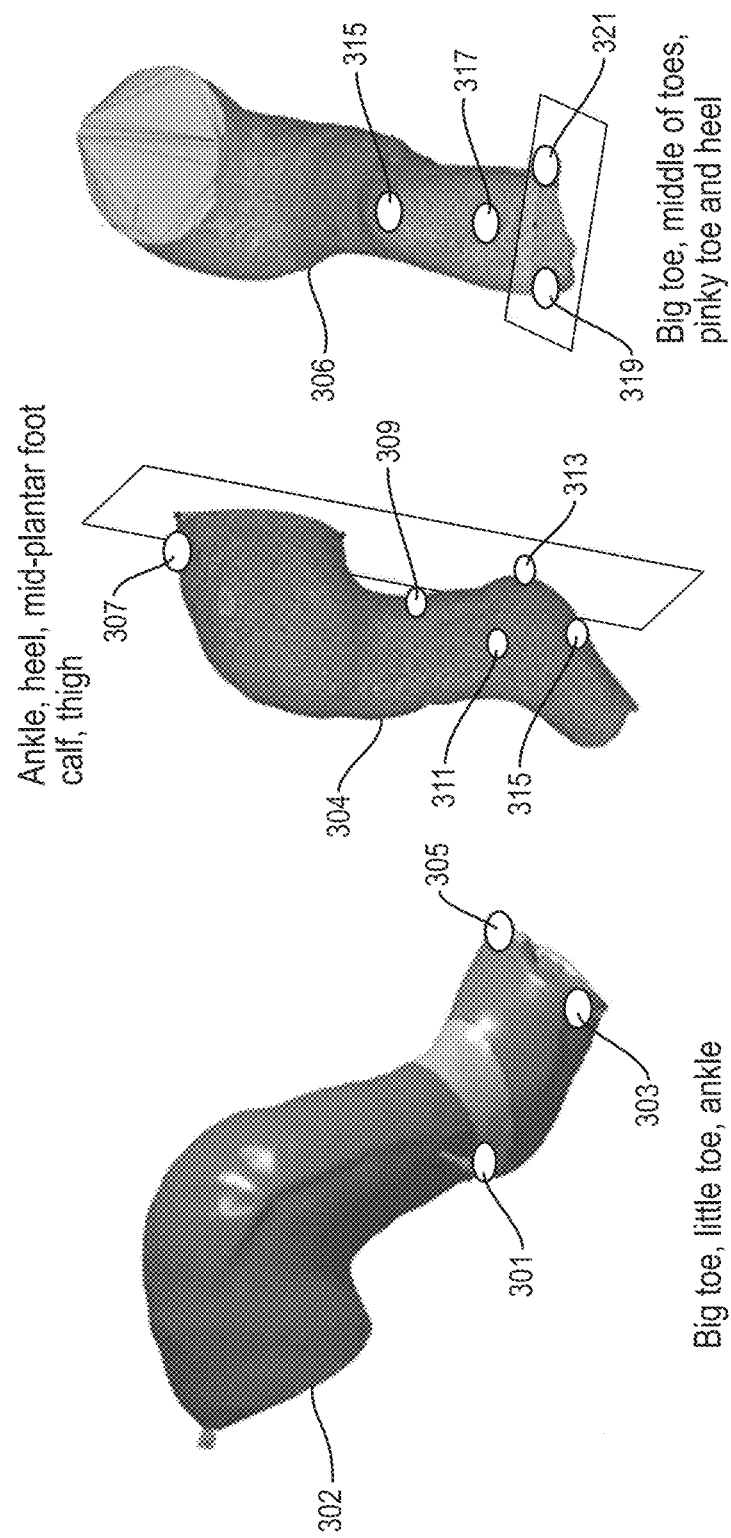
FIGS. 3A and 3B are illustrations of selecting reference points and determining the planes for correction in accordance with various embodiments taught herein.
Figure 3B:
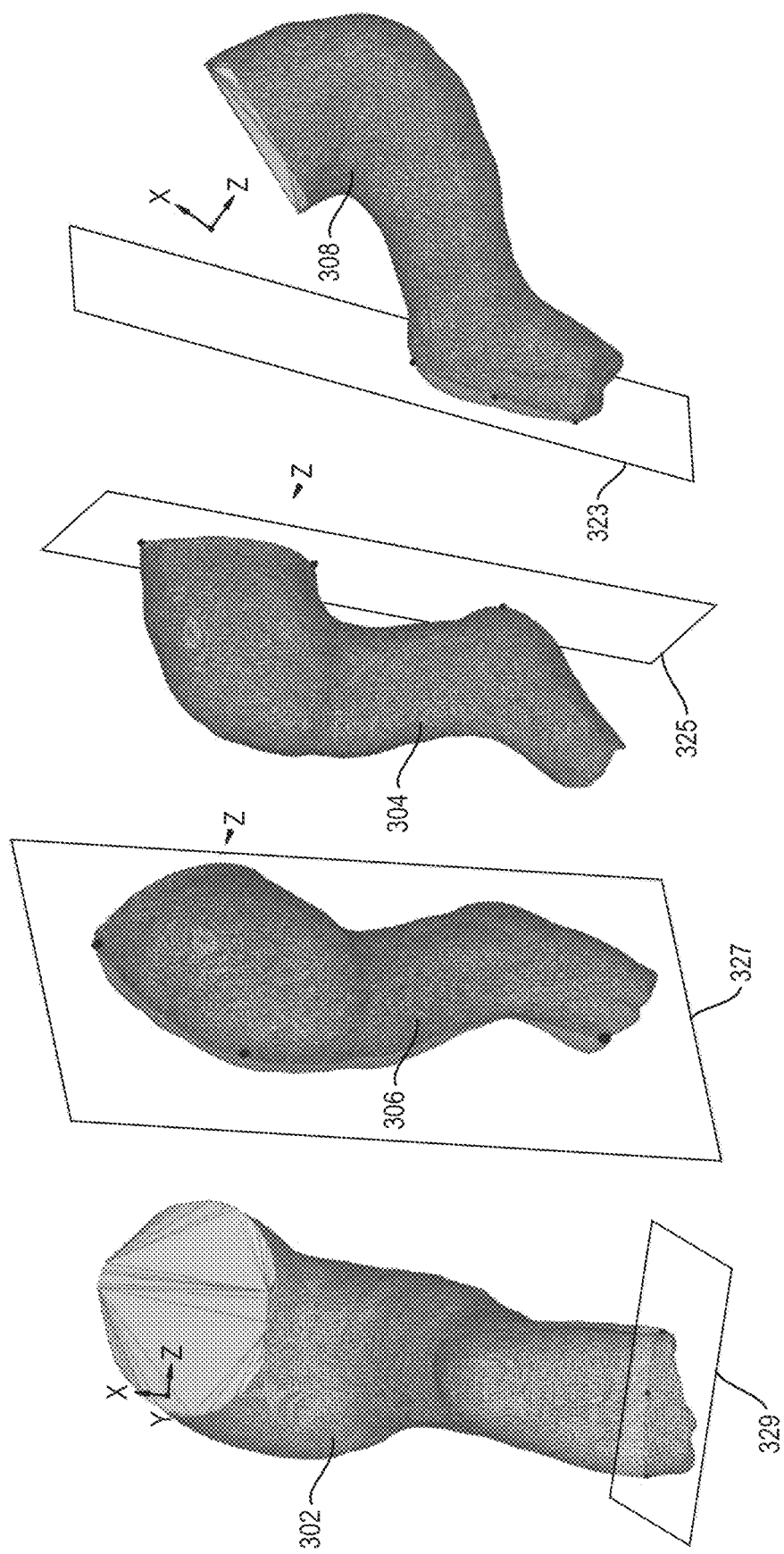
Figure 3C:
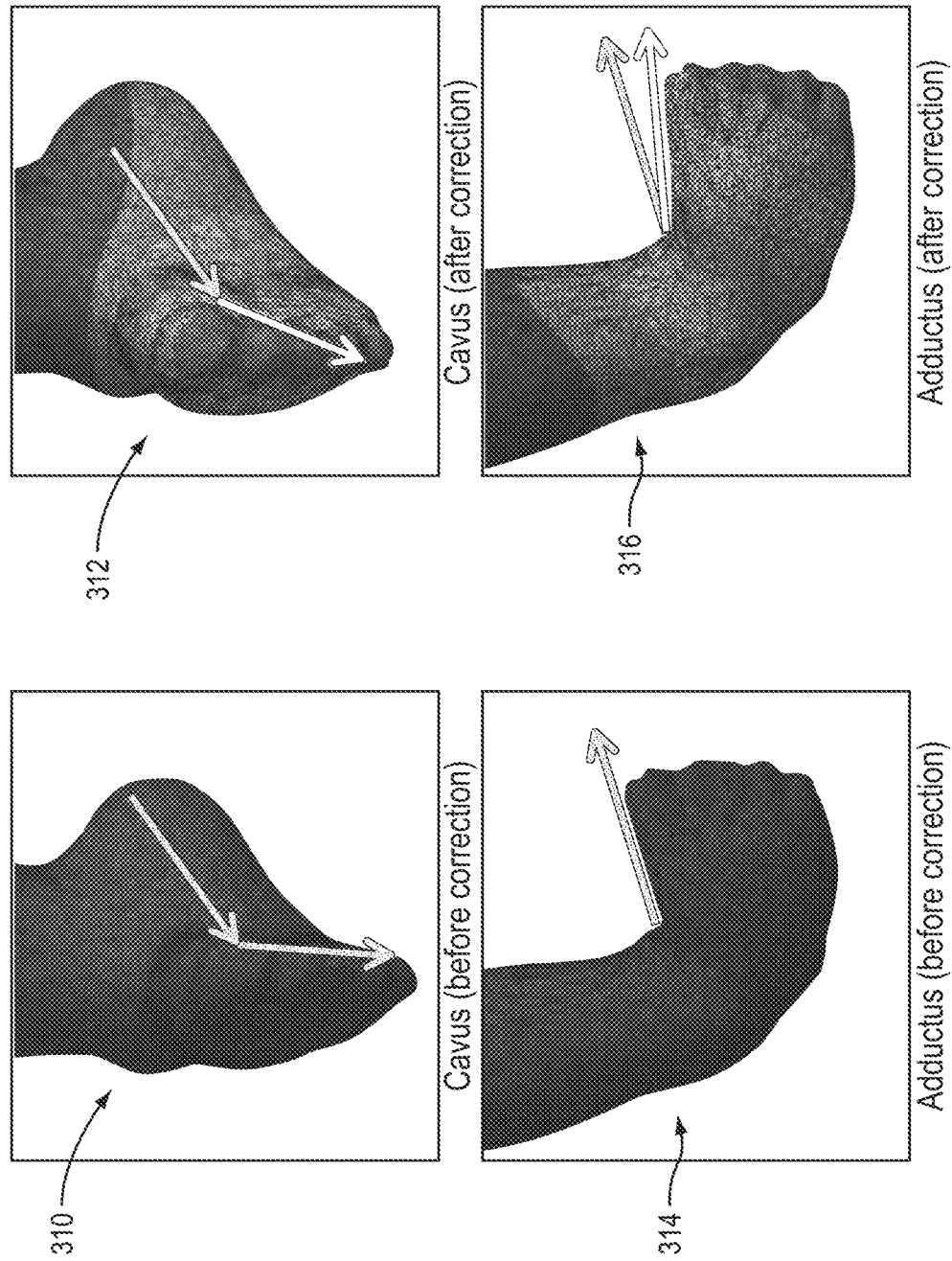
FIGS. 3C, 3D, and 3E are illustrations of corrections of deformities using finite element analysis in accordance with various embodiments taught herein.
Figure 3D:
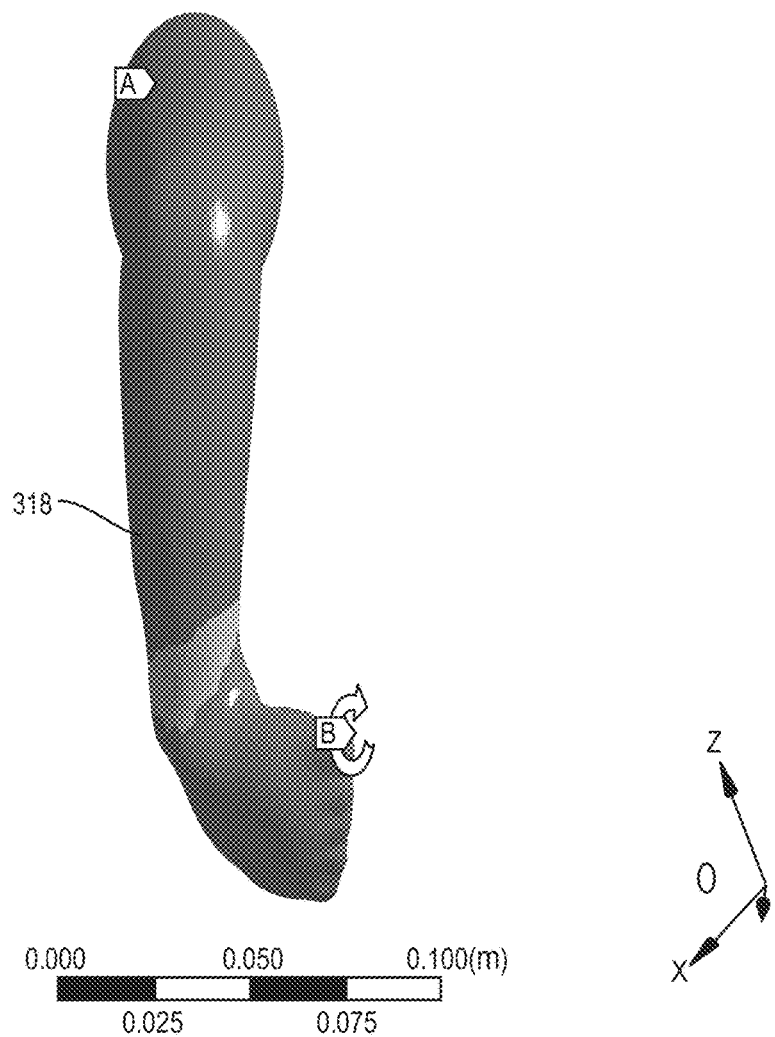
Figure 3E:
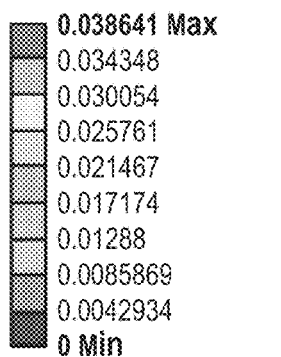
Figure 3E:
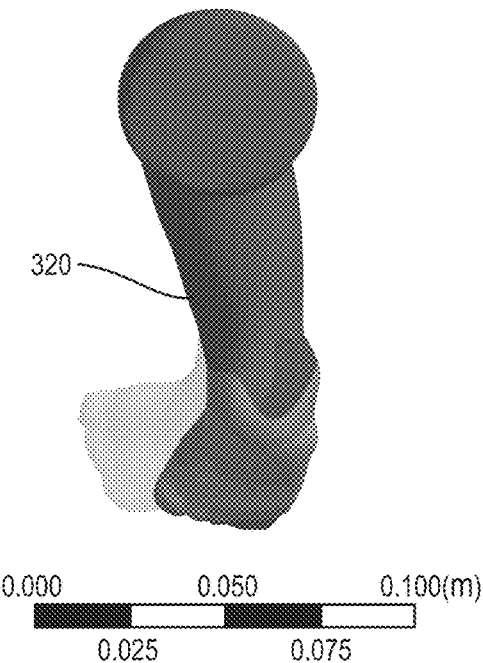
Figure 3E:
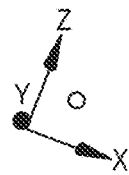
Figure 3E:
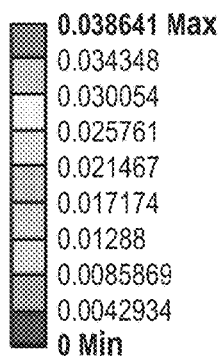
Figure 3E:
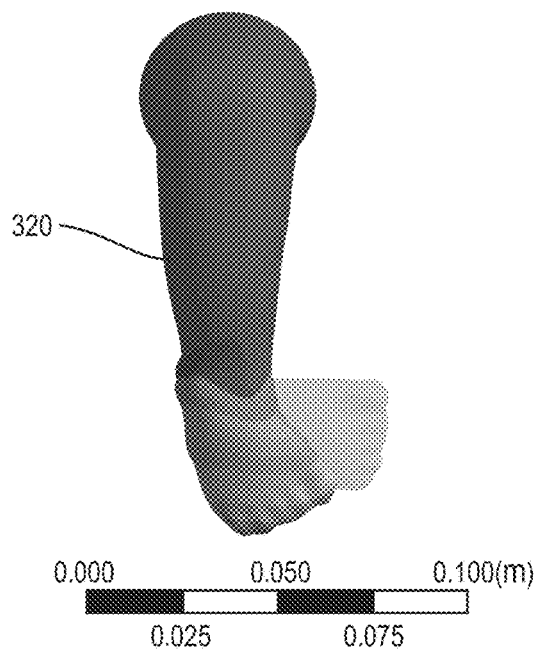
Figure 3E:
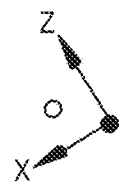

Referring now to FIGS. 3A, 3B, 3C, and 3D the system 100 can determine the reference points for generating the corrective plane. FIGS. 3A and 3B illustrates the reference points for generating the corrective planes. FIG. 3C illustrates before correction cavus image 310 and after correction cavus image 312 generated by the system 100 using finite element analysis. FIG. 3C also illustrates the before correction Adductus image 314 and the after correction Adductus image 316 generated by the system 100 using finite element analysis. FIG. 3D and FIG. 3E illustrates the before correction Varus image 318 and the after correction Varus image 320 (from two different points of view) generated by the system 100 using finite element analysis.

In an exemplary embodiment, the system 100 can determine the reference points for an adductus deformity based on the big toe 305, little toe 303, and ankle 301 as shown in a three-dimensional image of the adductus deformity 302 in FIG. 3A. In an exemplary embodiment, the system 100 can use these reference points to generate the reference plane 323 as shown in FIG. 3B. The system 100 can use the reference plane 323 to determine the force vectors to correct the adductus deformity 314, 316 as shown in FIG. 3C.

The system 100 can determine the reference points for correcting an equinus deformity based on the ankle 311, heel 313, mid plantar of foot 315, and thigh 307 as shown in a three-dimensional image of the equinus deformity 304 as shown in FIG. 3A. In an exemplary embodiment, the system 100 can use these reference points to generate the reference plane 325 to determine the force vectors to correct the equinus deformity as shown in FIG. 3B. The system 100 can then determine the force vector or set of force vectors to correct an equinus deformity based on the reference plane 327.

The system 100 can determine the reference points for correcting a cavus deformity based on the big toe 319, middle of toes 317, pinky toe 321 and heal 315 as shown in a three-dimensional image of the cavus deformity 306 in FIG. 3A. The system 100 can determine the reference plane 323 based on these reference points as shown in FIG. 3B. The system 100 can then determine the force vector or set of force vectors to correct the cavus deformity 310, 312 as shown in FIG. 3C.

The corresponding FIG. 3B illustrates identification of four different planes using these reference points shown in FIG. 3A. In an exemplary embodiment, system 100 can determine these reference points using image processing algorithm or a machine learning algorithm that recognizes features of the limb. In an exemplary embodiment, the machine learning model can be trained on deformed foot to identify these features.

Figure 4A:
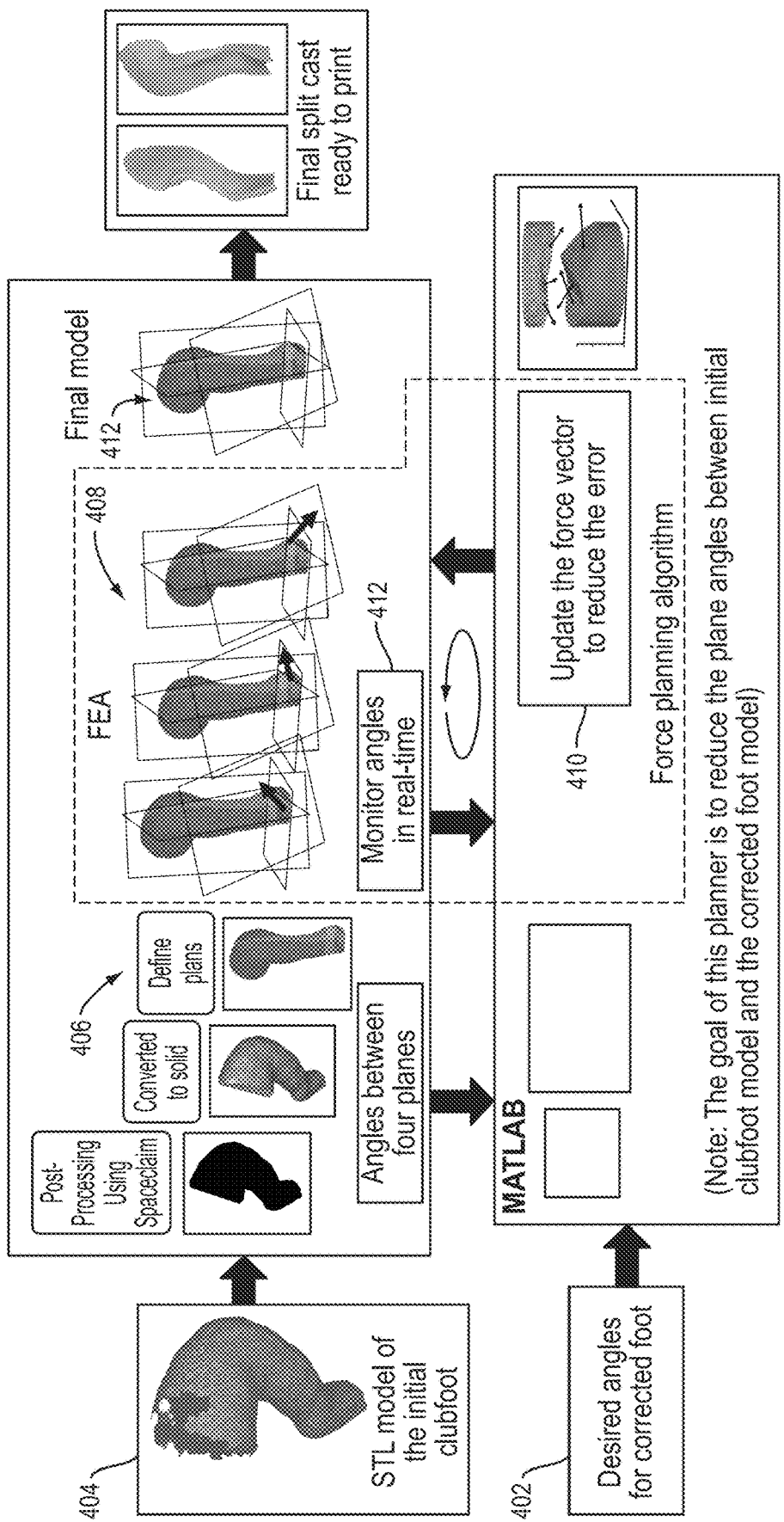
FIG. 4A is an illustration of the process of determining a next cast in a series of casts based on the three-dimensional image of the deformity and the boundary conditions in accordance with various embodiments taught herein.
Figure 4B:
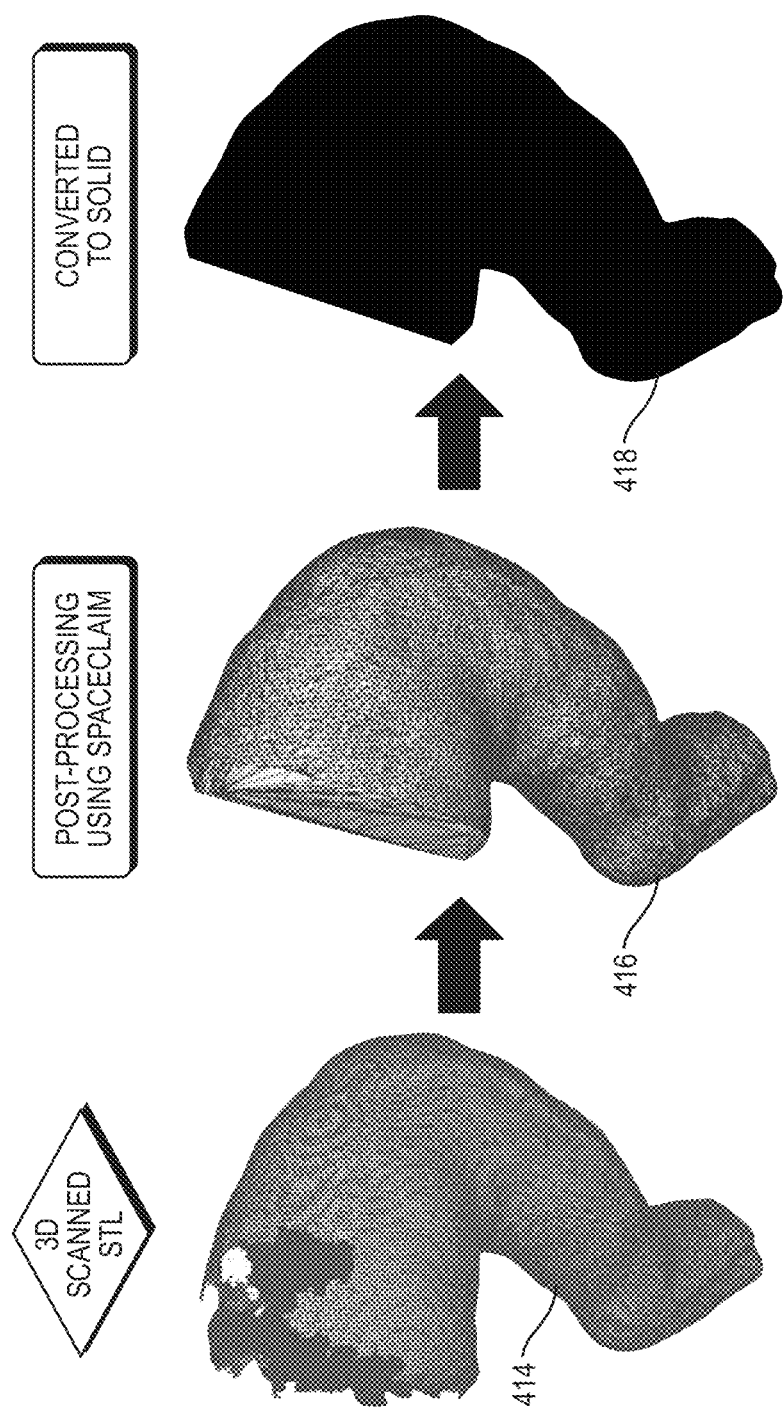
FIG. 4B is an illustration of the post-processing in accordance with the various embodiments taught herein.
Figure 4C:
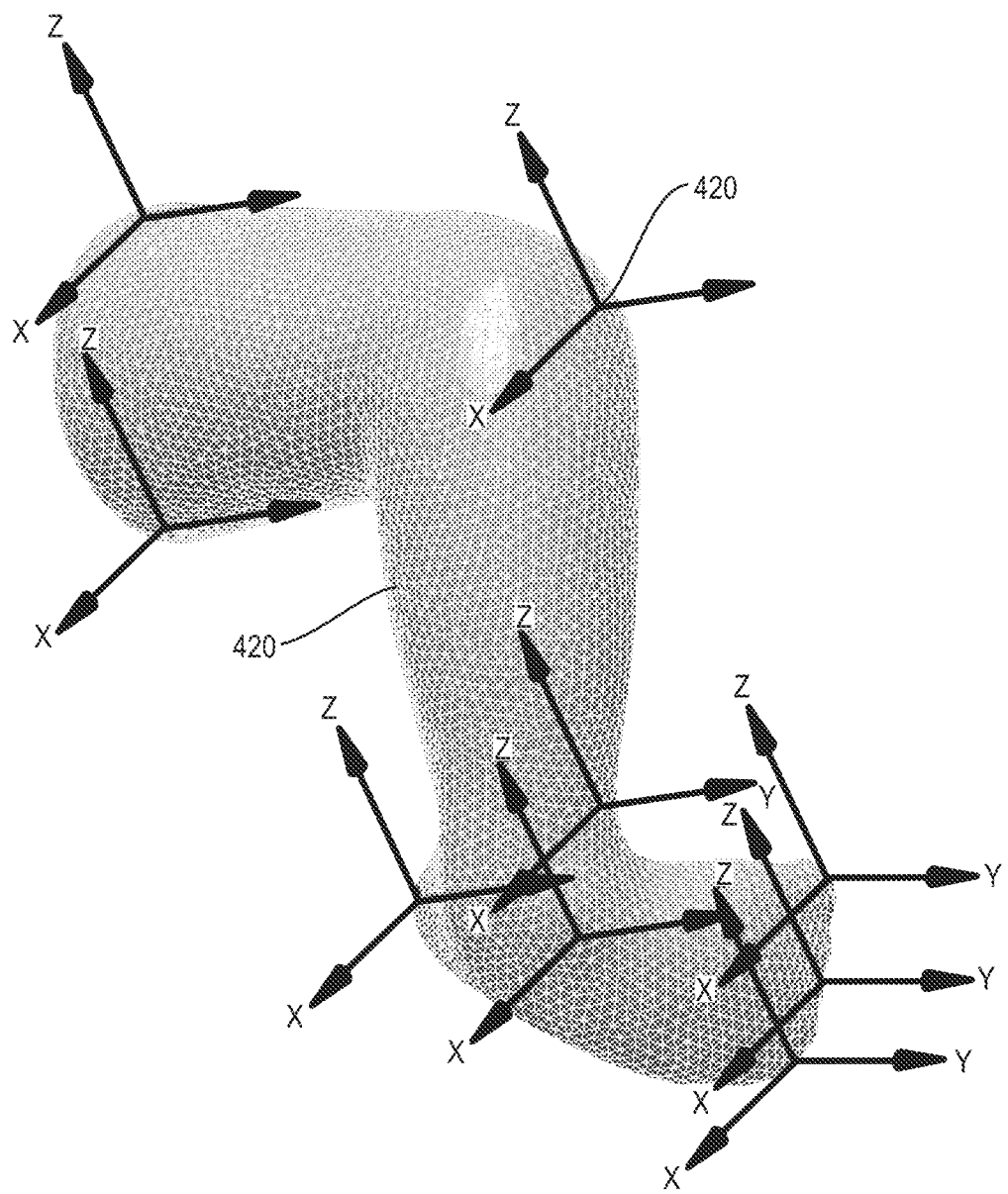
FIG. 4C is an illustration of force vectors at selected reference points in accordance with the various embodiments taught herein.

With reference to FIGS. 4A, 4B and 4C, the system 100 can be configured to determine the boundary conditions of the deformity based on a machine learning model. In an exemplary embodiment, the boundary conditions of the deformity can be the desired angles for corrected foot 402. FIG. 4A illustrates the process of generating a final model of force vectors for correcting a deformity based on the boundary conditions and the 3d model of the deformity. FIG. 4B illustrates the process of generating a solid model based on 3d scans. FIG. 4C illustrates the force vectors at the reference points determined by the system 100 in accordance with an exemplary embodiment described herein.

The system 100 can obtain a three-dimensional image or data 404 of the deformity. In exemplary embodiments, the system 100 can generate a three-dimensional model of the deformity either as a solid object or as a point cloud. FIG. 4B illustrates a method of generating a three-dimensional solid object in a modelling software based on the images of the foot. The system 100 can convert the three-dimensional scan images of the deformity into an STL file 414. The system 100 can then post-process the STL file 414 to fill in any missing information using a post-processing tool (e.g., Spacclaim). The system 100 can then convert the post-processed file into a solid three-dimensional object in the modelling software for further analysis.

Returning to FIG. 4A, the system 100 can determine multiple separate planes for the deformity as shown in 406 to serve as a reference between the position of the deformity and the expected or normal mean position of the limb or other appendage. The system 100 can select the number of planes based on the geometry of the deformity, the degrees of freedom of the deformity, the deviation of the deformity from a statistical normal limb or appendage and the like. In an exemplary embodiment, the system 100 can determine the reference points as described above with reference to FIG. 3A-3E. In an exemplary embodiment, the system 100 can select four different planes based on a machine learning model for club foot. In another example, the four planes can be selected with inputs from a doctor. The system 100 can use the machine learning trainer 114 to determine a four plane machine learning model that identifies the appropriate planes to use for correction.

For example, the machine learning trainer 114 can use data from a plurality of prior patients that includes planes that were selected for correction for the patients compared and the geometry of the deformity and the outcome of the corrective effort. The system 100 can then fit the three-dimensional data 404 of the deformity based on the trained four plane machine learning model. Once the four planes are identified the system 100 can use finite element analysis 408 to determine the force vectors for correcting the deformity in each plane.

In an exemplary embodiment, the system 100 can determine the force vectors at the reference points as illustrated in FIG. 4A and FIG. 4C using finite element analysis. The system 100 can determine the force vectors 422 as shown in FIG. 4C at the reference points for correcting the deformity. In an exemplary embodiment, the system 100 can apply a corrective force and determine the predicted correction such as the predicted angles for the corrected foot based on the applied force. The system 100 can then compare it with the boundary conditions such as desired angles for the corrected foot. The system 100 can iterate or simulate 410 for various force corrections then update the force vectors to reduce the error or minimize the error.

In an exemplary embodiment, the system 100 can use the boundary conditions 402 and the angle between the four planes and the boundary conditions 402 to determine the force vectors required during finite element analysis for correcting the deformity in each plane and generating for the next cast in the series of casts. In an exemplary embodiment the system 100 can determine the angle between the four planes using the modelling tools (e.g., Ansys, Matlab or both). Although the FIG. 4A illustrates the use of two modelling tools (e.g., Ansys and Matlab), to perform the various methods, in an exemplary embodiment the system 100 can use one or more modelling tools to perform the various methods.

For example, the system 100 can use the boundary conditions to iterate through a series of force vectors to minimize the error between the boundary condition and the results of applying a particular force vector in a particular plane. The system 100 can run a series of simulations using a trial correction and then determine the probable corrected deformity. The system 100 can as shown in the FIG. 4A iterates over a number of simulations until a force vector or a set of force vectors for the next series cast such as final model 412 is obtained. The system can determine the force vector or set of force vectors with the minimum deviation from the boundary condition using the iterative process. In an exemplary embodiment when the angle between the boundary conditions 402 and the probable corrected deformity is minimal the error is minimum. In an exemplary embodiment the system 100 can track the angle between the boundary condition and the predicted or estimated corrected plane if a force vector or set of force vectors is applied for each simulation in real-time 412.

In an exemplary embodiment, the system 100 can generate data for split casts based on the final model 412. In an exemplary embodiment, the split cast can include a portion that is not changed during at least a part of the series of casts and a portion that is updated during the next cast in the series of casts.

In exemplary embodiments, the system 100 can use the machine learning trainer 114 to determine the finite element analysis machine learning model. The finite element analysis machine learning model can be based force vectors that correspond to points in the point cloud determined from prior simulations for a plurality of prior patients. For example, the data for the plurality of prior patients can include the force vectors generated using simulations for a next cast in a series of casts, the boundary conditions used to arrive at the force vectors and the correction achieved as evident from the subsequent three-dimensional image of the deformity after it was corrected with the cast can be used to train the finite element analysis machine learning model. In exemplary embodiments, the finite element analysis machine learning model can generate a force vector or a set of force vectors for a cast or a series of casts based on the boundary conditions given manually or obtained from the finite element analysis machine learning model.

The system 100 can run supervised learning, unsupervised learning, reinforcement learning algorithms or any combination thereof. Examples of machine learning algorithms that can be implemented via the computing device 112 can include, but are not limited to Linear Regression, Logical Regression, Decision Tree, Support Vector Machine, Naïve Bayes, k-Nearest Neighbors, k-Means, Random Forest, Dimensionality Reduction algorithms such as GBM, XGBoost, LightGBM and CatBoost.

Examples of supervised learning algorithms that can be used in the computing device 112 can include regression, decision tree, random forest, k-Nearest Neighbors, Support Vector Machine, and Logic Regression. Examples of unsupervised learning algorithms that may be used in the computing device 112 include apriori algorithm and k-means. Examples of reinforcement learning algorithms that may be used in computing device 112 includes a Markov decision process.

Figure 5:
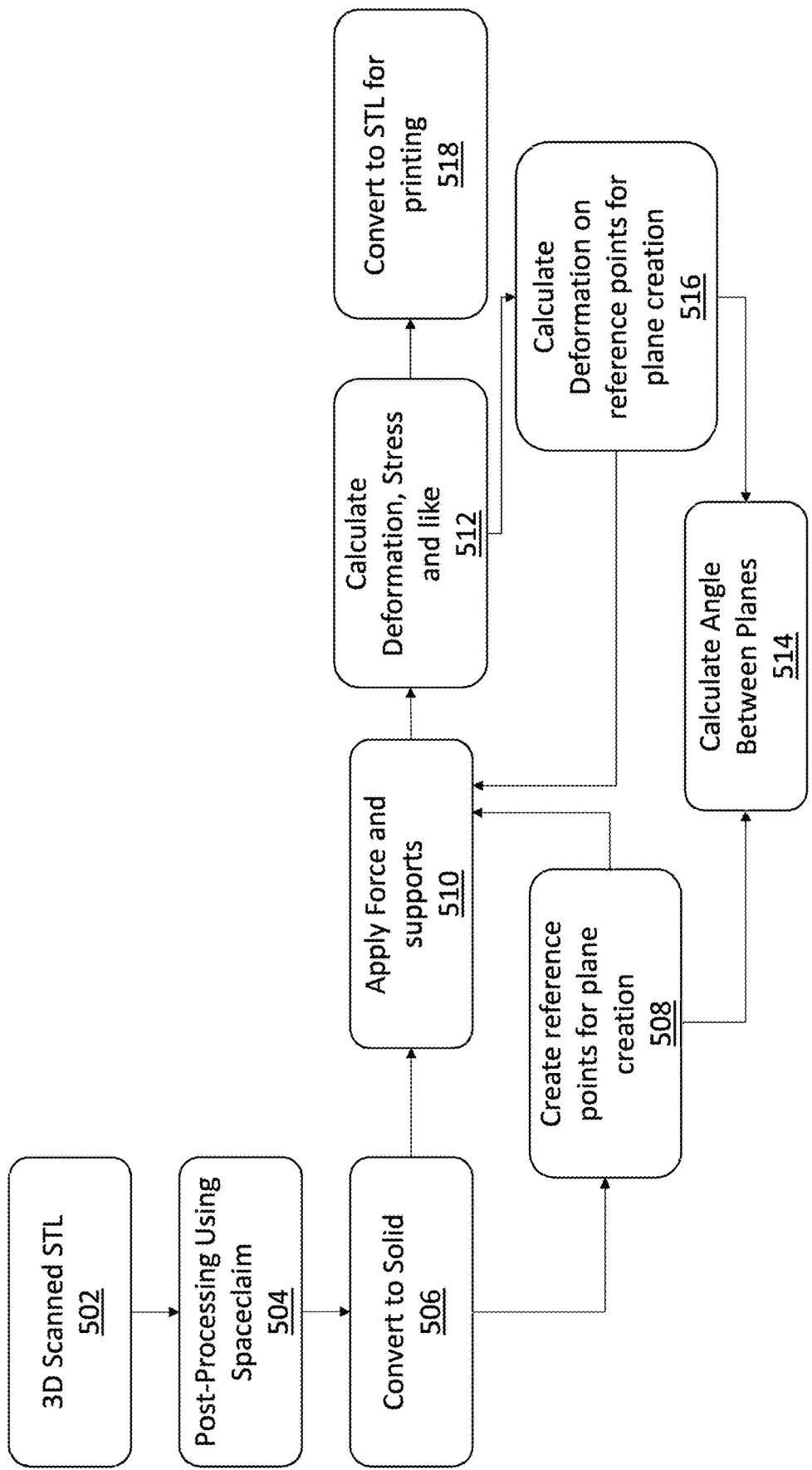
FIG. 5 is an illustration a finite element analysis modelling in accordance with various embodiments taught herein.

Referring to FIG. 5, the system 100 can apply finite element analysis manually. At step 502, the system 100 can generate a three-dimensional scanned stereolighography (STL) file based on the three-dimensional image from the camera 102. At step 504, the STL file can be post processed to clean up any irregularities. For example, the system 100 can remove any imperfections in the STL file such as from motion during capture of the three-dimensional image using image processing algorithms. At step 506, the system 100 can convert the three-dimensional image to a three-dimensional solid model. For example, the system 100 can use the multiple points present in the STL file and generate a solid shape of the deformity that are connected using extrapolations to generate a surface instead of multiple discrete points. At step 508, the system 100 can create reference points for generating the planes for finite element analysis of the force vector or set of force vectors to be applied to the deformity to correct the deformity. In an exemplary embodiment, the system 100 can receive a selection of reference points for generating a correction plane from the doctor. In another example, a machine learning algorithm can select the reference points based on a trained machine learning model as described herein above. At step 510, the system 100 can simulate the application of the force vector to the deformity and the effect of the force vector on the points of support for the deformity. At step 512, the system 100 can calculate the deformation and the stresses when the force vector is applied. For example, the system 100 can determine the deformation of the deformity and the stresses on the deformity when the force vector or set of force vectors is applied via a cast. At step 516, the system can calculate the deformation on the reference points for plane creation. For example, the system 100 can determine the deformation on the chosen reference points in the deformity to determine the effect of the force vectors on the deformity. At step 514, the system 100 can calculate the angle between the planes of the selected reference place and the desired boundary condition 502. At step 518, the system can convert the generated final model data into a next cast in the series of casts. The system 100 can convert the final model into an STL file for three-dimensional printing.

Figure 6A:
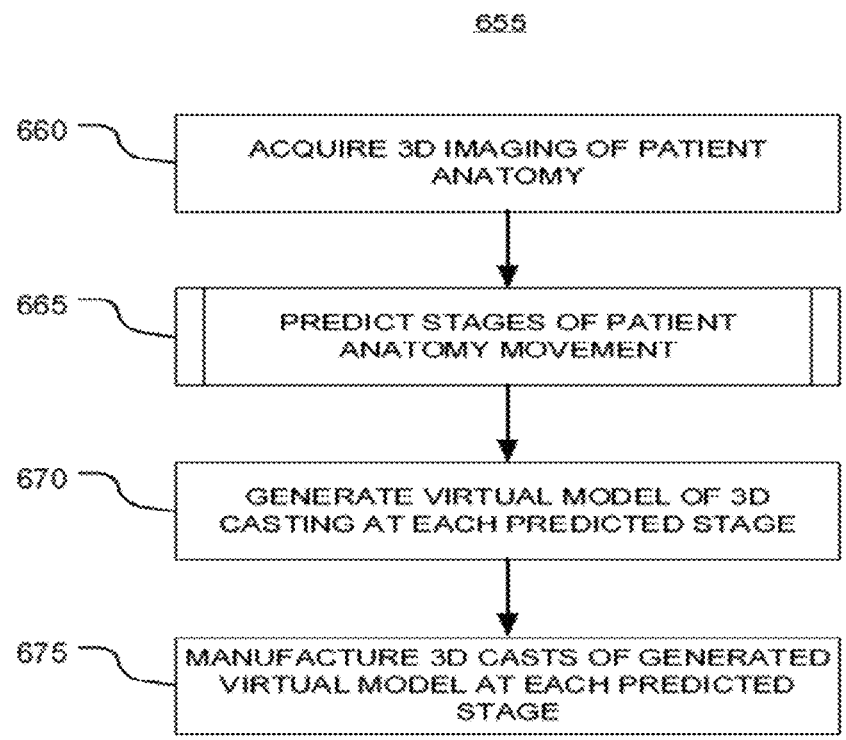
FIG. 6A illustrates a flowchart for image acquisition of the deformity and generation of a predicted virtual casting model in accordance with various embodiments taught herein.

Referring now to FIG. 6A, the method of the present disclosure will now be described with reference to the flowchart. At step 660, of process 655, three-dimensional images of the deformity can be acquired. In an embodiment, the three-dimensional images of the deformity can be acquired by a mobile device of a parent. The three-dimensional imaging can include depth mapping of the foot of the patient. In an embodiment, the three-dimensional imaging can include ultrasound for the determination of internal biological structures of the foot. In an exemplary embodiment, the combination of the two above-described three-dimensional imaging modalities allows for improved cast planning by considering the internal structures in addition to the outward appearance.

At sub process 665 of process 655 and based upon the acquired three-dimensional images of the patient anatomy, casting stages of patient anatomy movement can be predicted. The casting stages can be predicted via the force vector modeling described herein above. In one instance, this prediction can include computer predictive modeling and finite element analysis of the foot wherein stresses, deformations of the structures of the foot or both are considered from one stage to the next. Sub process 665 will be further described with reference to FIG. 6B. At step 670 of process 655, virtual models of three-dimensional casts can be generated for anticipated patient anatomy movements at each predicted stage. Such virtual models of three-dimensional casts can allow for visualization and modification according to real-world constraints. At step 675, of process 650, three-dimensional casts, similar to that of FIG. 5, can be generated for each virtual model at each predicted stage of patient anatomy movement.

Figure 6B:
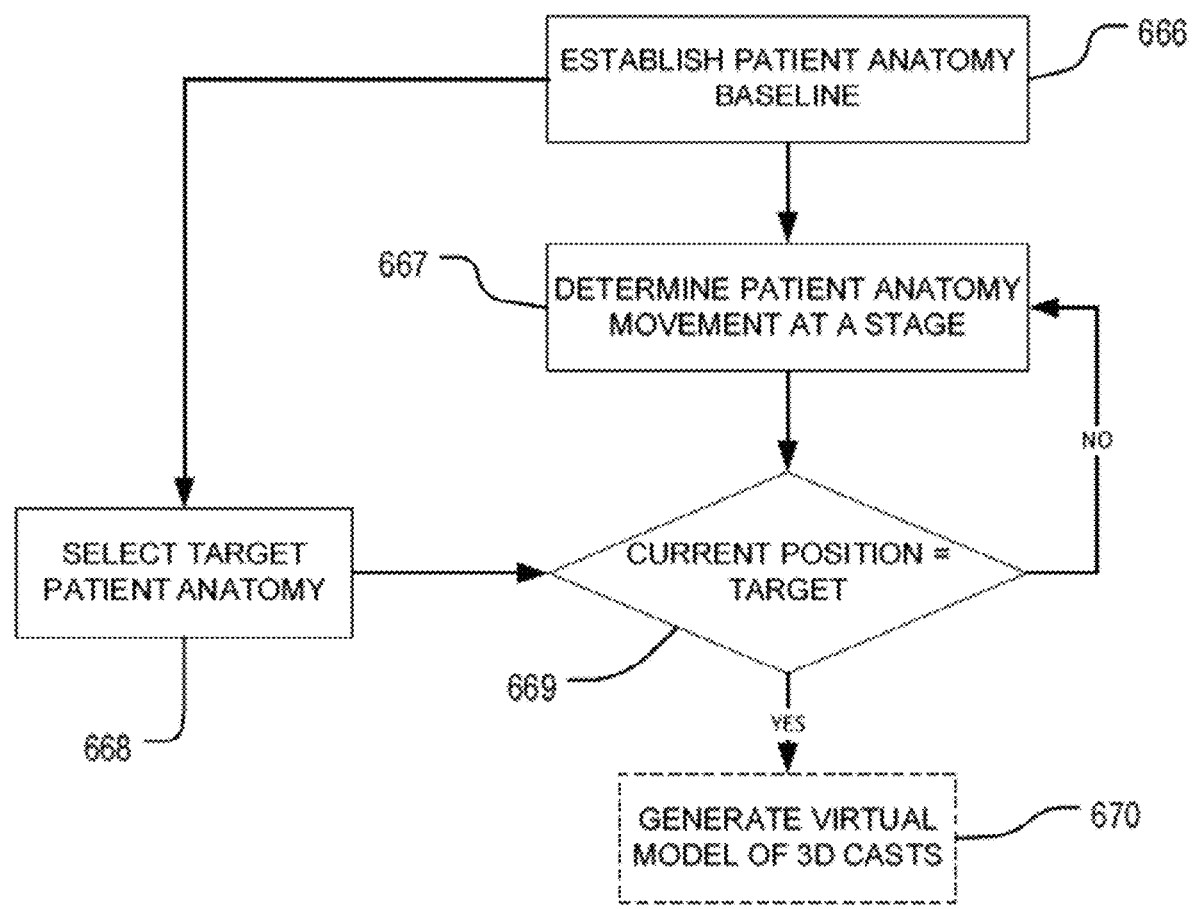
FIG. 6B illustrates a flow chart for determining the number of stages and trajectory of the predicted movement in accordance with various embodiments taught herein.

With reference to FIG. 6B, sub process 665 of process 655 includes determining the number of stages and trajectory of each predicted stage of movement. At step 666, of sub process 665, a baseline patient anatomy can be established according to the acquired images of the patient anatomy.

Accordingly, at step 668 of sub process 665, a target patient anatomy can be selected, the target being an end goal shape of the structure of the foot.

At step 667 of sub process 665, the patient anatomy movement at each stage can be determined. This determination can include movements of structures of the foot. In an embodiment, such movements can be determined in the context of the Ponseti stages and include, for instance, performing specific angular rotations at specific stages. In an embodiment, such movements can be optimized at each stage such that maximum movement is achieved without creating undue mechanical and/or biological stresses. For instances, each stage may be determined such that von Mises stress, for instance, remain below a threshold value.

At step 669, of sub process 665, the current position of the patient anatomy can be compared with the target patient anatomy position from step 668. If the two values are equal, for instance, only a single stage of casting may be required and the determined patient anatomy movement can be used to generate a virtual model of a necessary three-dimensional cast at step 670. If, however, the current position and the target patient anatomy do not match, a successive stage of patient anatomy movement is required and the sub process 665 returns to step 667.

According to an embodiment, in this way, the number of stages, or cast, required to be fitted to a patient is dependent upon the severity of the deformity and the ability to move the patient anatomy at each stage. In the case of clubfoot, this can mean the difference of manufacturing four casts in one instance and six casts in another, thereby allowing each patient to receive only the minimum necessary number of casts.

According to an embodiment, the above described method of FIG. 6A and FIG. 6B can be performed with only external features gathered via, for instance, depth mapping data. External features can be processed similarly to Schoenecker, et al., Systems and methods for serial treatment of a muscular-skeletal deformity, U.S. Patent Application Publication No. US2017/0091411 A1, incorporated herein by reference.

According to an embodiment, the external features can be applied to a machine learning algorithm in order to generate patient anatomy predictions without need for ultrasound imaging. For instance, a library of corresponding images of a foot may be stored.

The corresponding images can include images of the external features of the foot and corresponding images of the internal features of the foot. In this way, the machine learning algorithm, a convolutional neural network in exemplary embodiment, can be trained to correlate external features with internal features. Therefore, when provided with an external feature of an unknown foot, the machine learning algorithm can generate a corresponding internal feature structure that can be used in determining patient anatomy movements during stage planning. The library of corresponding images can be a corpus of patient data acquired from patients of a similar diagnosis and healthy patients.

Figure 7:
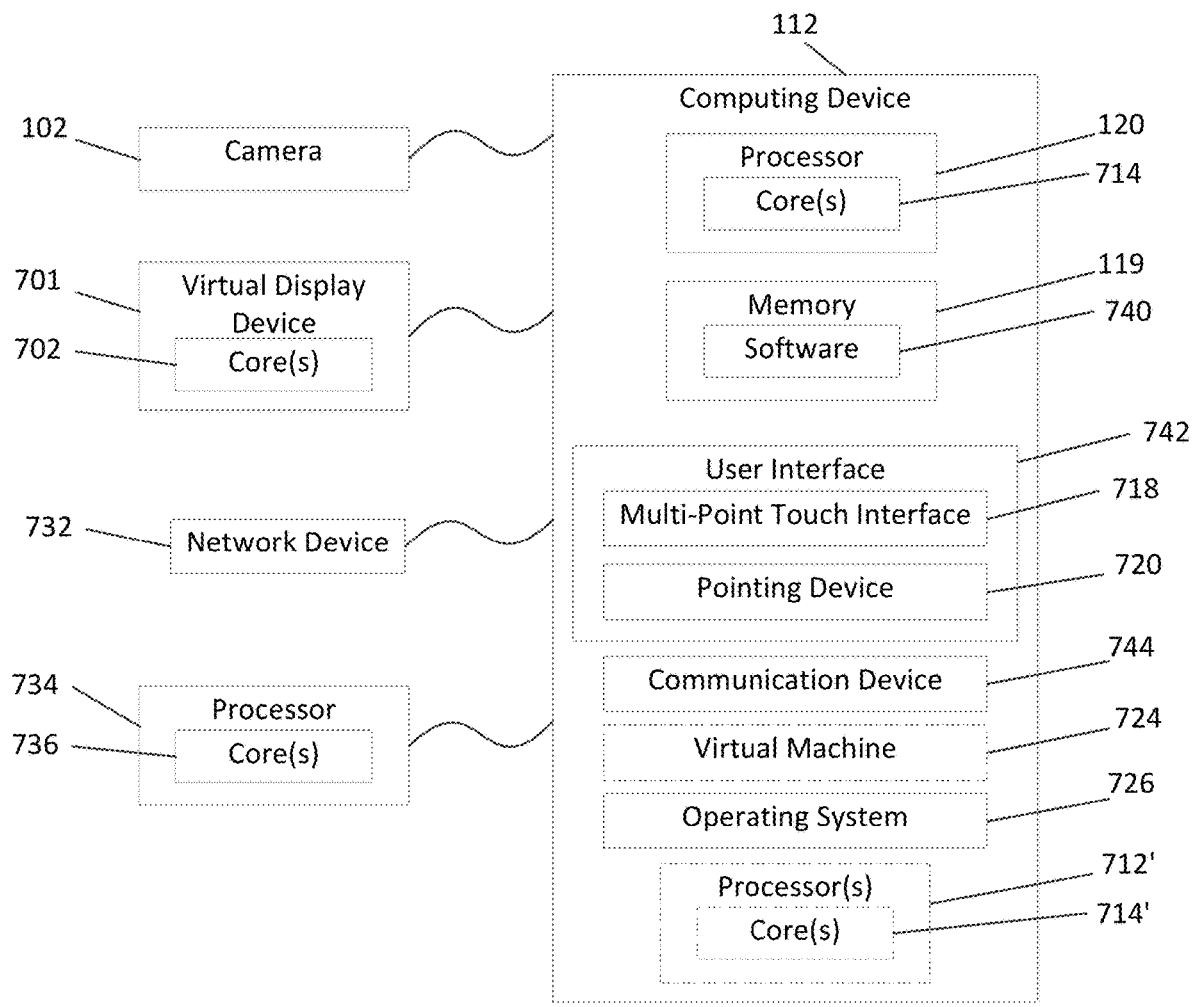
FIG. 7 illustrates an exemplary computing system for determining the force vectors for correcting a deformity in accordance with various embodiments taught herein.

FIG. 7 is a block diagram of an exemplary embodiment of computing device 112 in accordance with embodiments of the present disclosure. The computing device 112 can include one or more non-transitory computer-readable media for storing one or more computer-executable instructions or software for implementing exemplary embodiments. The non-transitory computer-readable media can include, but are not limited to, one or more types of hardware memory, non-transitory tangible media (for example, one or more magnetic storage disks, one or more optical disks, one or more flash drives), and the like. For example, memory 119 included in the computing device 112 can store computer-readable and computer-executable instructions or software for performing the operations disclosed herein. For example, the memory 119 can store a software application 640 which is configured to perform several of the disclosed operations (e.g., the pre-training platform for determining the co-occurrence matrix, the training platform for determining the word vectors and the topic determination platform for determining the plurality of topics and the representative noun). The computing device 610 can also include configurable, programmable processor 120 or both and an associated core(s) 614, and optionally, one or more additional configurable, programmable processing devices or both, e.g., processor(s) 612' and associated core(s) 614' (for example, in the case of computational devices having multiple processors/cores), for executing computer-readable and computer-executable instructions or software application 640 stored in the memory 119 and other programs for controlling system hardware. Processor 120 and processor(s) 612' can each be a single-core processor or multiple core (614 and 614') processor.

Virtualization can be employed in the computing device 610 so that infrastructure and resources in the computing device can be shared dynamically. A virtual machine 624 can be provided to handle a process running on multiple processors so that the process appears to be using only one computing resource rather than multiple computing resources. Multiple virtual machines can also be used with one processor.

Memory 119 can include a computational device memory or random access memory, such as DRAM, SRAM, EDO RAM, and the like. Memory 119 can include other types of memory as well, or combinations thereof.

A user can interact with the computing device 710 (shown in FIG. 1 as 112) through a visual display device 701, such as a computer monitor, which can display one or more user interfaces 742 that can be provided in accordance with exemplary embodiments. The computing device 710 can include other I/O devices for receiving input from a user, for example, a keyboard or any suitable multi-point touch interface 718, a pointing device 720 (e.g., a mouse). The keyboard and the pointing device 720 can be coupled to the visual display device 701. The computing device 710 can include other suitable conventional I/O peripherals.

The computing device 710 can also include one or more storage devices such as a hard-drive, CD-ROM, or other computer readable media, for storing data and computer-readable instructions, software that perform operations disclosed herein or both. Exemplary storage device 734 can also store one or more databases for storing any suitable information required to implement exemplary embodiments. The databases can be updated manually or automatically at any suitable time to add, delete, update one or more items in the databases.

The computing device 710 can include a communication device 744 configured to interface via one or more network devices 732 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The communication device 744 can include a built-in network adapter, network interface card, PCMCIA network card, card bus network adapter, wireless network adapter, USB network adapter, modem, radio frequency transceiver, or any other device suitable for interfacing the computing device 710 to any type of network capable of communication and performing the operations described herein. Moreover, the computing device 710 can be any computational device, such as a workstation, desktop computer, server, laptop, handheld computer, tablet computer, or other form of computing or telecommunications device that is capable of communication and that has sufficient processor power and memory capacity to perform the operations described herein.

The computing device 710 can run any operating system 726, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 726 can be run in native mode or emulated mode. In an exemplary embodiment, the operating system 726 can be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts and that the steps in the exemplary flowcharts may be performed in a different order than the order shown in the illustrative flowcharts.

What is claimed is:

1. A system for modeling of force vectors for a cast to correct an orthopedic deformity, the system comprising:
   a processor programmable to execute machine readable instructions on one or more non-transitory media holding the machine readable instructions, the processor configured to:
   receive an image of the deformity;
   generate a three-dimensional model of the deformity based on the image of the deformity;
   determine boundary conditions of the deformity using a machine learning model executable by the processor, wherein the machine learning model is trained using a corpus of prior images of orthopedic deformities of patients;
   simulate, using a finite element analysis, an application of a force vector to the three-dimensional model of the deformity and the effect thereon on points of support; and
   generate a set of force vectors for a cast based on a series of automated finite-element-analysis simulations to minimize a deviation from the determined boundary condition.

2. The system of claim 1, wherein the corpus of prior images of the orthopedic deformity of patients includes an uncorrected image of the deformity of the patients, one or more intermediate images of the deformity of the patients and an image of the final corrected deformity of the patient.

3. The system of claim 1, wherein the system includes a camera.

4. The system of claim 3, wherein the camera is at least one of, an array of cameras, an ultrasound, a three-dimensional scanner, an magnetic resonance imaging device, or a CT scanner.

5. The system of claim 1, wherein the corpus of prior images of patients includes a plurality of scans of prior discarded casts of patients to determine the original deformity, the stages of correction of the deformity and the final corrected deformity.

6. The system of claim 1, wherein to generate the set force vectors for the cast the system is programmed to:
   process the finite element analysis based on force vectors that correspond to one or more points in a point cloud of the deformity generated from one or more prior simulations for a plurality of patients; and
   determine the set of force vectors for the cast using the finite element analysis.

7. The system of claim 1, wherein to generate the set force vectors for the cast the system is programmed to:
   correct the deformity in more than one direction in the cast simultaneously.

8. The system of claim 1, wherein to generate the set force vectors for the cast the system is programmed to:
   correct the deformity simultaneously in three dimensions for each plane of correction.

9. A method for modeling of force vectors for serial casts to correct orthopedic deformities, the method comprising:
   receiving, via a computing device, an image of the deformity;
   generating, via the computing device, a three-dimensional model of the deformity based on the image of the deformity;
   determining, via the computing device, boundary conditions of the deformity using a machine learning model, the machine learning model is trained using a corpus of prior images of orthopedic deformities of patients or prior images of casts used to correct orthopedic deformities of the patients;
   simulating, using a finite element analysis, via the computing device, an application of a force vector to the three-dimensional model of the deformity and the effect thereon on points of support; and
   generating, via the computing device, a set force vectors for a cast based on a series of automated finite-element-analysis simulations to minimize a deviation from the determined boundary condition.

10. The method of claim 9, wherein the image of the deformity is acquired via a camera.

11. The method of claim 10, wherein the camera is at least one of an array of cameras, an ultrasound, a three-dimensional scanner, an magnetic resonance imaging device, or a CT scanner.

12. The method of claim 9, wherein the corpus of prior images of patients includes a plurality of scans of prior discarded casts of patients to determine the original deformity, the stages of correction of the deformity and the final corrected deformity.

13. The method of claim 9, wherein the method further comprises:
processing the finite element analysis based on force vectors that correspond to one or more points in a point cloud of the deformity based on prior simulations for a plurality of patients.

14. A non-transitory computer readable medium storing instructions executable by a processing device, wherein execution of the instructions causes the processing device to implement a method for modeling of force vectors for a cast to correct an orthopedic deformities, the method comprising:
generating, via the computing device, a three-dimensional model of the deformity based on the image of the deformity;
determining, via the computing device, boundary conditions of the deformity using a machine learning model, wherein the machine learning model is trained using a corpus of prior images of orthopedic deformities of patients;
simulating, using a finite element analysis, via the computing device, an application of a force vector to the three-dimensional model of the deformity and the effect thereon on points of support; and
generating, via the computing device, a set of force vectors for a cast based on a series of automated finite-element-analysis simulations to minimize a deviation from the determined boundary condition.

* * * * *